United States Patent
Ulanet et al.

(10) Patent No.: US 12,290,508 B2
(45) Date of Patent: *May 6, 2025

(54) METHODS OF USE FOR TRISUBSTITUTED BENZOTRIAZOLE DERIVATIVES

(71) Applicant: Servier Pharmaceuticals LLC, Boston, MA (US)

(72) Inventors: Danielle Ulanet, Cambridge, MA (US); Sung Eun Choe, Lexington, MA (US)

(73) Assignee: Servier Pharmaceuticals LLC, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/207,887

(22) Filed: Jun. 9, 2023

(65) Prior Publication Data

US 2024/0148697 A1 May 9, 2024

Related U.S. Application Data

(63) Continuation of application No. 16/971,199, filed as application No. PCT/US2019/018472 on Feb. 19, 2019, now Pat. No. 11,717,512.

(51) Int. Cl.
*A61K 31/4192* (2006.01)
*A61P 35/00* (2006.01)

(52) U.S. Cl.
CPC .......... *A61K 31/4192* (2013.01); *A61P 35/00* (2018.01)

(58) Field of Classification Search
CPC ............................ A61K 31/4192; A61P 35/00
See application file for complete search history.

(56) References Cited

U.S. PATENT DOCUMENTS

| | | |
|---|---|---|
| 6,841,561 B1 | 1/2005 | Tan et al. |
| 9,630,932 B2 | 4/2017 | Thunuguntla et al. |
| 9,937,155 B2 | 4/2018 | Hosahalli |
| 10,080,740 B2 | 9/2018 | Thunuguntla et al. |
| 11,147,801 B2 | 10/2021 | Nellore et al. |
| 11,717,512 B2 * | 8/2023 | Ulanet ................ A61P 35/00 514/359 |
| 2006/0199856 A1 | 9/2006 | Leban et al. |
| 2008/0287503 A1 | 11/2008 | Petry et al. |
| 2012/0028959 A1 | 2/2012 | Thunuguntla et al. |
| 2013/0035329 A1 | 2/2013 | Saunders et al. |
| 2013/0109643 A1 | 5/2013 | Riggins et al. |
| 2013/0295198 A1 | 11/2013 | Claudio et al. |
| 2017/0224663 A1 | 8/2017 | Nellore et al. |
| 2018/0263970 A1 | 9/2018 | Sykes et al. |
| 2018/0369206 A1 | 12/2018 | Nellore et al. |
| 2019/0025313 A1 | 1/2019 | Si et al. |
| 2019/0105304 A1 | 4/2019 | Thunuguntla et al. |
| 2019/0151326 A1 | 5/2019 | Lindmark et al. |
| 2021/0088520 A1 | 3/2021 | Si et al. |
| 2022/0055995 A1 | 2/2022 | Altaf et al. |
| 2022/0241246 A1 | 8/2022 | Nellore et al. |
| 2023/0285364 A1 | 9/2023 | Coco et al. |
| 2023/0285365 A1 | 9/2023 | Coco et al. |

FOREIGN PATENT DOCUMENTS

| | | |
|---|---|---|
| CN | 102348689 A | 2/2012 |
| CN | 103476770 A | 12/2013 |
| CN | 103965133 A | 8/2014 |
| EP | 3019482 B1 | 8/2018 |
| JP | 2004-536122 A | 12/2004 |
| JP | 2007-015952 A | 1/2007 |
| JP | 2012-520251 A | 9/2012 |
| JP | 2012-520252 A | 9/2012 |
| JP | 2013-513613 A | 4/2013 |
| JP | 2020-517654 A | 6/2020 |
| RU | 2374256 C2 | 11/2009 |
| TW | I372758 B | 9/2012 |
| TW | 201902880 A | 1/2019 |
| WO | WO-1996/35419 A1 | 11/1996 |
| WO | 2001/24785 A2 | 4/2001 |
| WO | WO-2003/006425 A2 | 1/2003 |
| WO | WO-2006/024034 A1 | 3/2006 |
| WO | WO-2008/028860 A1 | 3/2008 |
| WO | WO-2010/081898 A1 | 7/2010 |

(Continued)

OTHER PUBLICATIONS

Akbay et al., D-2-hydroxyglutarate produced by mutant IDH2 causes cardiomyopathy and neurodegeneration in mice. Genes Dev. Mar. 1, 2014;28(5):479-90.
Al-Soud et al., Synthesis and properties of new substituted 1,2,4-triazoles: potential antitumor agents. Bioorg Med Chem. Apr. 17, 2003;11(8):1701-8.
Arnould et al., Checkpoint kinase 1 inhibition sensitises transformed cells to dihydroorotate dehydrogenase inhibition. Oncotarget. Jul. 12, 2017;8(56):95206-95222.
Batt, Inhibitors of dihydroorotate dehydrogenase. Expert Opinion on Therapeutic Patents. 1999;9(1):41-54.
Baumann et al., Dihydroorotate dehydrogenase inhibitor A771726 (leflunomide) induces apoptosis and diminishes proliferation of multiple myeloma cells. Mol Cancer Ther. Feb. 2009;8(2):366-75.
Borodovsky et al., 5-azacytidine reduces methylation, promotes differentiation and induces tumor regression in a patient-derived IDH1 mutant glioma xenograft. Oncotarget. Oct. 2013;4(10):1737-47.

(Continued)

*Primary Examiner* — Paul V Ward
(74) *Attorney, Agent, or Firm* — McCarter & English, LLP; Wei Song

(57) ABSTRACT

The present invention provides methods for treating cancer in a subject with a trisubstituted benzotriazole derivative with the formula (I)

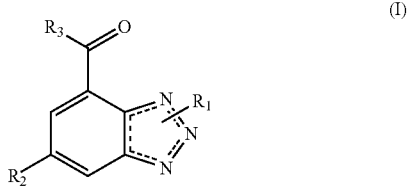

or a pharmaceutically acceptable salt thereof, wherein the variables $R_1$, $R_2$ and $R_3$ are as defined herein.

5 Claims, 7 Drawing Sheets

(56) References Cited

FOREIGN PATENT DOCUMENTS

| WO | 2010/102825 A1 | 9/2010 |
|---|---|---|
| WO | WO-2010/115736 A2 | 10/2010 |
| WO | WO-2011/072174 A1 | 6/2011 |
| WO | WO-2013/049112 A1 | 4/2013 |
| WO | WO-2014/128669 A2 | 8/2014 |
| WO | WO-2015/130728 A1 | 9/2015 |
| WO | WO-2015/169944 A1 | 11/2015 |
| WO | WO-2017/037022 A1 | 3/2017 |
| WO | 2018/077923 A1 | 5/2018 |
| WO | WO-2018/136009 A1 | 7/2018 |
| WO | WO-2018/197997 A1 | 11/2018 |
| WO | WO-2019/012030 A1 | 1/2019 |
| WO | WO-2019/164794 A1 | 8/2019 |
| WO | WO-2020/067412 A1 | 4/2020 |
| WO | WO-2020/109625 A1 | 6/2020 |
| WO | WO-2020/132471 A1 | 6/2020 |
| WO | WO-2021/062157 A1 | 4/2021 |
| WO | WO-2021/262874 A1 | 12/2021 |
| WO | WO-2022/047051 A1 | 3/2022 |

OTHER PUBLICATIONS

Brown et al., Adaptive Reprogramming of De Novo Pyrimidine Synthesis Is a Metabolic Vulnerability in Triple-Negative Breast Cancer. Cancer Discov. Apr. 2017;7(4):391-399.
Cao et al., Targeting of Hematologic Malignancies with PTC299, A Novel Potent Inhibitor of Dihydroorotate Dehydrogenase with Favorable Pharmaceutical Properties. Mol Cancer Ther. Jan. 2019;18(1):3-16.
Castelli et al., New Developments of Differentiation Therapy of Acute Myeloid Leukemia. Current Pharmacogenomics and Personalized Medicine. 2016;14(2):86-105.
Chandrashakara, The treatment strategies of autoimmune disease may need a different approach from conventional protocol: a review. Indian J Pharmacol. Nov.-Dec. 2012;44(6):665-71.
Chaturvedi et al., Mutant IDH1 promotes leukemogenesis in vivo and can be specifically targeted in human AML. Blood. Oct. 17, 2013;122(16):2877-87.
Chemistry Explained, Isomerism. Retrieved online at: http://www.chemistryexplained.com/Hy-Kr/Isomerism.html. 4 pages, (2016).
Christian et al., The novel dihydroorotate dehydrogenase (DHODH) inhibitor BAY 2402234 triggers differentiation and is effective in the treatment of myeloid malignancies. Leukemia. Oct. 2019;33(10):2403-2415.
Damia, Targeting DNA-PK in cancer. Mutation Research/Fundamental and Molecular Mechanisms of Mutagenesis. 2020;821;111692, 7 pages.
Dang et al., Cancer-associated IDH1 mutations produce 2-hydroxyglutarate. Nature. Dec. 10, 2009;462(7274):739-44.
Dexter et al., Activity of a novel 4-quinolinecarboxylic acid, NSC 368390 [6-fluoro-2-(2'- fluoro-1, 1'-biphenyl-4-yl)-3-methyl-4-quinolinecarboxylic acid sodium salt], against experimental tumors. Cancer Res. Nov. 1985;45(11 Pt 1):5563-8.
Dunleavy, Aggressive B cell Lymphoma: Optimal Therapy for MYC-positive, Double-Hit, and Triple-Hit DLBCL. Curr Treat Options in Oncol. 2015;16:58, 11 pages.
Elsayed et al., Prognostic value of IDH1 mutations identified with PCR-RFLP assay in acute myeloid leukemia patients. J Egypt Natl Canc Inst. Mar. 2014;26(1):43-9.
Emadi et al., Presence of isocitrate dehydrogenase mutations may predict clinical response to hypomethylating agents in patients with acute myeloid leukemia. Am J Hematol. May 2015;90(5):E77-9.
Golub et al., Molecular classification of cancer: class discovery and class prediction by gene expression monitoring. Science. Oct. 15, 1999;286(5439):531-7.
Jin et al., Cancer-associated IDH1 and IDH2 mutations: therapeutic opportunities. EJC Supplement. Nov. 17, 2010;8(7):56. Poster 160.

Kinnaird et al., Metabolic modulation of cancer: a new frontier with great translational potential. J Mol Med (Berl). Feb. 2015;93(2):127-42.
Koundinya et al., Dependence on the Pyrimidine Biosynthetic Enzyme DHODH Is a Synthetic Lethal Vulnerability in Mutant KRAS-Driven Cancers. Cell Chem Biol. Jun. 21, 2018;25(6):705-717.
Ladds et al., A DHODH inhibitor increases p53 synthesis and enhances tumor cell killing by p53 degradation blockage. Nat Commun. Mar. 16, 2018;9(1):1107.
Li et al., The effects of teriflunomide on lymphocyte subpopulations in human peripheral blood mononuclear cells in vitro. J Neuroimmunol. Dec. 15, 2013;265(1-2):82-90.
Liu et al., Structures of human dihydroorotate dehydrogenase in complex with antiproliferative agents. Structure. Jan. 15, 2000;8(1):25-33.
Lolli et al., Use of human Dihydroorotate Dehydrogenase (hDHODH) Inhibitors in Autoimmune Diseases and New Perspectives in Cancer Therapy. Recent Pat Anticancer Drug Discov. 2018;13(1):86-105.
Luengo et al., Targeting Metabolism for Cancer Therapy. Cell Chem Biol. Sep. 21, 2017;24(9):1161-1180.
Madak et al., Revisiting the role of dihydroorotate dehydrogenase as a therapeutic target for cancer. Pharmacol Ther. Mar. 2019;195:111-131. Pre-publication edition.
Mathur et al., PTEN Regulates Glutamine Flux to Pyrimidine Synthesis and Sensitivity to Dihydroorotate Dehydrogenase Inhibition. Cancer Discov. Apr. 2017;7(4):380-390.
Matsuda et al., Distinct global DNA methylation status in B-cell lymphomas: immunohistochemical study of 5-methylcytosine and 5-hydroxymethylcytosine. J Clin Exp Hematop. 2014;54(1):67-73.
McDonald et al., Selective Vulnerability to Pyrimidine Starvation in Hematologic Malignancies Revealed by AG-636, a Novel Clinical-Stage Inhibitor of Dihydroorotate Dehydrogenase. Mol Cancer Ther. Dec. 2020;19(12):2502-2515.
McLean et al., Multiple inhibitor analysis of the brequinar and leflunomide binding sites on human dihydroorotate dehydrogenase. Biochemistry. Feb. 20, 2001;40(7):2194-200.
Munier-Lehmann et al., On dihydroorotate dehydrogenases and their inhibitors and uses. J Med Chem. Apr. 25, 2013;56(8):3148-67.
NIH—National Cancer Institute, Targeted Cancer Therapies. Retrieved online at: http://www.cancer.gov/aboutcancer/treatment/types/targetedtherapies/targetedtherapiesfactsheet. 6 pages, Apr. 25, 2014.
Ravandi et al., Prognostic significance of alterations in IDH enzyme isoforms in patients with AML treated with high-dose cytarabine and idarubicin. Cancer. May 15, 2012;118(10):2665-73.
Ringshausen et al., The immunomodulatory drug Leflunomide inhibits cell cycle progression of B-CLL cells. Leukemia. Mar. 2008;22(3):635-8.
Rohle et al., An inhibitor of mutant IDH1 delays growth and promotes differentiation of glioma cells. Science. May 3, 2013;340(6132):626-30.
Ruckemann et al., Leflunomide inhibits pyrimidine de novo synthesis in mitogen-stimulated T-lymphocytes from healthy humans. J Biol Chem. Aug. 21, 1998;273(34):21682-91.
Schenkein, Agios at J.P. Morgan Healthcare Conference. Slideshow, 34 pages, Jan. 8, 2018.
Sun et al., Targeting the pyrimidine synthesis pathway for differentiation therapy of acute myelogenous leukemia. Translational Cancer Research. Feb. 28, 2017;6:S109-S111.
Sykes et al., Inhibition of Dihydroorotate Dehydrogenase Overcomes Differentiation Blockade in Acute Myeloid Leukemia. Cell. Sep. 22, 2016;167(1):171-186.e1-e8.
Turcan et al., Efficient induction of differentiation and growth inhibition in IDH1 mutant glioma cells by the DNMT Inhibitor Decitabine. Oncotarget. Oct. 2013;4(10):1729-36.
Ullrich et al., Recombinant expression of N-terminal truncated mutants of the membrane bound mouse, rat and human flavoenzyme dihydroorotate dehydrogenase. A versatile tool to rate inhibitor effects? Eur J Biochem. Mar. 2001;268(6):1861-8.
Vyas et al., Recent developments in the medicinal chemistry and therapeutic potential of dihydroorotate dehydrogenase (DHODH) inhibitors. Mini Rev Med Chem. Oct. 2011;11(12):1039-55.

(56) References Cited

OTHER PUBLICATIONS

Walse et al., The structures of human dihydroorotate dehydrogenase with and without inhibitor reveal conformational flexibility in the inhibitor and substrate binding sites. Biochemistry. Aug. 26, 2008;47(34):8929-36.
Wang et al., Targeted inhibition of mutant IDH2 in leukemia cells induces cellular differentiation. Science. May 3, 2013;340(6132):622-6.
Woo et al., The antilymphocytic activity of brequinar sodium and its potentiation by cytidine. Effects on lymphocyte proliferation and cytokine production. Transplantation. Aug. 1993;56(2):374-81.
Yamaguchi et al., IDH1 and IDH2 mutations confer an adverse effect in patients with acute myeloid leukemia lacking the NPM1 mutation. Blood. 2013;122(21):4977.
Zeng et al., Targeting dihydroorotate dehydrogenase in acute myeloid leukemia. Haematologica. Sep. 2018;103(9):1415-1417.
International Search Report and Written Opinion for Application No. PCT/US2019/018472, dated Apr. 1, 2019, 8 pages.
U.S. Appl. No. 14/784,708, filed Oct. 15, 2015, U.S. Pat. No. 9,630,932, Issued.
U.S. Appl. No. 15/494,820, filed Apr. 24, 2017, U.S. Pat. No. 9,937,155, Issued.
U.S. Appl. No. 15/718,961, filed Sep. 28, 2017, U.S. Pat. No. 10,080,740, Issued.
U.S. Appl. No. 15/899,707, filed Feb. 20, 2018, 2018-0369206, Abandoned.
U.S. Appl. No. 16/124,578, filed Sep. 7, 2018, 2019-0105304, Abandoned.
U.S. Appl. No. 16/066,984, filed Jun. 28, 2018, 2019-0025313, Abandoned.
U.S. Appl. No. 17/009,126, filed Sep. 1, 2020, 2021-0088520, Abandoned.
U.S. Appl. No. 16/971,199, filed Aug. 19, 2020, U.S. Pat. No. 11,717,512, Issued.
U.S. Appl. No. 17/416,910, filed Jun. 21, 2021, 2022-0055995, Published.
U.S. Appl. No. 18/012,136, filed Dec. 21, 2022, 2023-0285364, Published.
U.S. Appl. No. 18/015,396, filed Jan. 10, 2023, 2023-0285365, Published.
U.S. Appl. No. 16/607,607, filed Oct. 23, 2019, U.S. Pat. No. 11,147,801, Issued.
U.S. Appl. No. 17/501,701, filed Oct. 14, 2021, 2022-0241246, Published.
Anderson et al., Latest Medicinal Chemistry vol. 2, Technomic Co., Ltd., Japan. Sep. 25, 1999, pp. 347-365.
Bastin et al., Salt Selection and Optimisation Procedures for Pharmaceutical New Chemical Entities. Org Proc Res Dev. 2000;4(5):427-435.
Caira, Crystalline Polymorphism of Organic Compounds. Topics in Curren Chemistry, Design of Organic Solids. 1998;198:163-208.
Morissette et al., High-throughput crystallization: polymorphs, salts, co-crystals and solvates of pharmaceutical solids. Adv Drug Deliv Rev. Feb. 23, 2004;56(3):275-300.
Serajuddin et al., Salt formation to improve drug solubility. Adv Drug Deliv Rev. Jul. 30, 2007;59(7):603-16.

* cited by examiner

METHODS OF USE FOR TRISUBSTITUTED BENZOTRIAZOLE DERIVATIVES

CROSS-REFERENCE TO RELATED APPLICATION

This application is a continuation of U.S. patent application Ser. No. 16/971,199, filed Aug. 19, 2020, which is a 35 U.S.C. § 371 national stage filing of International Application No. PCT/US2019/018472, filed on Feb. 19, 2019, which in turn claims priority to International Patent Application No. PCT/US2018/018679, filed Feb. 20, 2018, which is incorporated herein by reference in its entirety.

BACKGROUND OF THE INVENTION

Field of the Invention

The present invention relates to methods of use of trisubstituted benzotriazole derivatives of formula (I), particularly methods of cancer treatment with these compounds.

Description of the Related Art

Lymphoma, leukemia, myeloma and myelodysplastic syndrome are the four main groups of blood or hematological cancers that are further divided into various subtypes. In the United States, it is estimated that one person in every three minutes is diagnosed with a hematological cancer and one person in every nine minutes dies from it.

Of note, acute monocytic leukemia is a distinct subtype of acute myeloid leukemia (AML) with characteristic clinical features of a patient having >20% blasts in the bone marrow, of which >80% are of the monocytic lineage. Acute monocytic leukemia has been reported to have a poor prognosis compared to other subtypes of AML, and it has been shown that the disease may develop after chemotherapy exposure, particularly following epipodophyllotoxins and anthracyclines.

Acute lymphoblastic leukemia (ALL), another leukemia subtype, is an aggressive hematologic malignancy wherein an abnormal proliferation of lymphoblasts suppresses normal hematopoiesis resulting in progressive marrow failure and death. This particular subtype has a bimodal age distribution with an initial peak in childhood and second that increases in older adults. While outcomes for ALL in children have improved with modern chemotherapy regimens, outcomes in adults remain dismal, which are attributable to a combination of increased adverse tumor biology and decreased tolerance of therapy. As a result despite a high initial remission rate most adults are destined to relapse. It has been declared that most adults with recurrent ALL "cannot be rescued with current therapies". This is likely the result of the fact that virtually all active therapies are used during first line treatment. There is clearly a need for additional active therapies in ALL.

A pioneering genetic evaluation of diffuse large B-cell lymphoma (DLBCL) reveals that the dual rearrangement of MYC and BCL2/BCL6 occurs in approximately 5% to 7% of patients with DLBCL. This form of DLBCL has recently been re-classified as "high-grade B-cell lymphoma, with MYC and BCL2 and/or BCL6 rearrangements", and is now commonly referred to as "double hit DLBCL" or "double hit lymphoma". Sometimes, all 3 genes MYC, BCL2 and BCL6—are simultaneously rearranged in a phenotype termed "triple hit DLBCL" or "triple hit lymphoma". Both double hit and triple hit lymphomas are highly proliferative and drug-resistant. Both phenotypes are also associated with an extremely poor prognosis with standard treatment, such as rituximab plus cyclophosphamide, doxorubicin, vincristine, and prednisone (R-CHOP)—all of which are suboptimal. Few patients with double hit lymphoma are cured with this approach. There are retrospective reviews suggesting that a more intensive therapy, such as etoposide, prednisone, vincristine, cyclophosphamide, and doxorubicin plus rituximab (EPOCH-R), may be better than standard treatment. For patients who are unable to undergo transplant, or for those who relapse after a stem cell transplant, the median survival is approximately 6 months.

With non-small cell lung cancer or carcinoma (NSCLC), which accounts for about 85% of all lung cancers, surgery is the mainstay of treatment. However, only a quarter of the patients undergo successful resection, with a recurrence rate of 50%. Therapeutic approaches in advanced disease involve, following surgery, both adjuvant chemotherapy and/or adjuvant radiotherapy, whereas chemotherapy as monotherapy (first-line therapy) seems to be an approach associated with relatively poor results. In a comparison of four commonly used combination chemotherapy regimens, none was superior. Response rates varied from 15% to 22%, with 1-year survival rates of 31% to 36%. Thus, even though pre-operative chemotherapy seems to have not resulted in a prolongation of life expectancy, adjuvant chemotherapy (also if combined with radiotherapy) did show a significant increase in life expectancy.

Despite an improvement in the median overall survival for patients with advanced ovarian cancer over the decades, the disease course is one of remission and relapse requiring intermittent re-treatment. The presence of cancer cells in effusions within the serosal (peritoneal, pleural, and pericardial) cavities is a clinical manifestation of advanced stage ovarian cancer and is associated with poor survival. Unlike the majority of solid tumors, particularly at the primary site, ovarian cancer cells in effusions are not amenable to surgical removal and failure in their eradication is one of the main causes of treatment failure.

In view of the foregoing, there remains an unmet need for new drugs that can treat aggressive lymphoma and leukemia subtypes more effectively, particularly forms of lymphoma that are refractory to standard therapy. There also exists a need for new drugs that can treat other hematological cancers that are relatively less known and understood, such as myelodysplastic syndrome and diffuse mixed cell lymphoma. In general, there is a continuing need for anti-cancer drugs with excellent potency, specificity and tolerability.

SUMMARY OF THE INVENTION

The present invention is directed to a method for treating a cancer selected from chemotherapy-resistant acute myeloid leukemia, cytarabine-resistant acute myeloid leukemia, acute monocytic leukemia, acute lymphoblastic leukemia, B-cell lymphoma, diffuse mixed cell lymphoma, myelodysplastic syndrome, primary effusion lymphoma, erythroleukemia, chronic myeloid leukemia, chronic monocytic leukemia, double hit diffuse large B cell lymphoma, triple hit diffuse large B cell lymphoma, biliary tract cancer or cancer of the ampulla of Vater, non-small cell lung cancer, bronchoalveolar carcinoma, liver cancer, cancer of the ovary, and cancer of the upper aerodigestive tract in a subject. The method comprises the step of administering to the subject one or more times a therapeutically effective amount of a compound represented by formula (I):

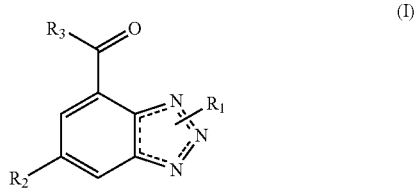

or a pharmaceutically acceptable salt thereof. In the structure, the dotted lines [ . . . ] in the ring represent an optional bond which is be present in any stable combination. $R_1$ is selected from hydrogen and alkyl; $R_2$ is -A-$R_4$; A is arylene or tetrasubstituted arylene; wherein the substituent is halogen; $R_3$ is selected from hydroxy and amino; $R_4$ is selected from an aryl and a heteroaryl that is optionally substituted with one or more $R_5$; and $R_5$ is selected from alkyl and —$(CH_2)_n$N($R_a$)$R_b$. $R_a$ and $R_b$ are independently selected from hydrogen, alkyl and —C(O)alkyl; alternatively $R_a$ and $R_b$ can be taken together with the nitrogen atom to which they are attached to form a 4-6 membered heterocyclyl containing 0-2 additional heteroatoms independently selected from O and N and is optionally substituted with alkyl. n is an integer selected from 0 and 1.

DETAILED DESCRIPTION OF THE INVENTION

Figure 1:
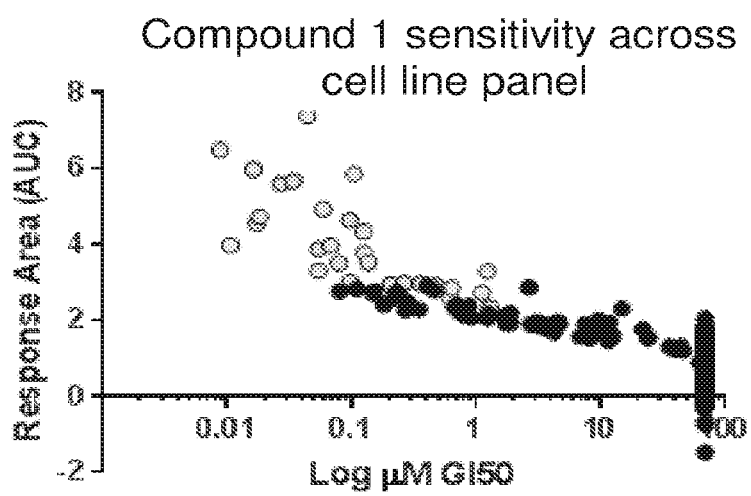
FIG. 1 shows the sensitivity of a panel of ~400 human cancer lines of hemapoietic and non-hemapoietic origin towards growth inhibition by Compound 1 of the invention.

The present invention further relates to a method for treating a cancer selected from chemotherapy-resistant acute myeloid leukemia, cytarabine-resistant acute myeloid leukemia, acute monocytic leukemia, acute lymphoblastic leukemia, diffuse mixed cell lymphoma, myelodysplastic syndrome, primary effusion lymphoma, erythroleukemia, chronic myeloid leukemia, chronic monocytic leukemia, B-cell lymphoma, double hit diffuse large B cell lymphoma, triple hit diffuse large B cell lymphoma, biliary tract cancer or cancer of the ampulla of Vater, non-small cell lung cancer, bronchoalveolar carcinoma, liver cancer, cancer of the ovary, and cancer of the upper aerodigestive tract in a subject, comprising the step of administering to the subject a therapeutically effective amount of a compound represented by formula (I) or a pharmaceutically acceptable salt thereof or a pharmaceutical composition comprising the same.

In one embodiment, the cancer treated in the method is chemotherapy-resistant acute myeloid leukemia. In one embodiment, the cancer treated in the method is cytarabine-resistant acute myeloid leukemia. In one embodiment, the cancer treated in the method is acute monocytic leukemia. In one embodiment, the cancer treated in the method is acute lymphoblastic leukemia. In one embodiment, the cancer treated in the method is diffuse mixed cell lymphoma. In one embodiment, the cancer treated in the method is myelodysplastic syndrome. In one embodiment, the cancer treated in the method is primary effusion lymphoma. In one embodiment, the cancer treated in the method is erythroleukemia. In one embodiment, the cancer treated in the method is chronic myeloid leukemia. In one embodiment, the cancer treated in the method is chronic monocytic leukemia. In one embodiment, the cancer treated in the method is B-cell lymphoma. In one embodiment, the cancer treated in the method is biliary tract cancer or cancer of the ampulla of Vater. In one embodiment, the cancer treated in the method is non-small cell lung cancer. In one embodiment, the cancer treated in the method is bronchoalveolar carcinoma. In one embodiment, the cancer treated in the method is liver cancer. In one embodiment, the cancer treated in the method is cancer of the ovary. In one embodiment, the cancer treated in the method is cancer of the upper aerodigestive tract.

As used herein, "chemotherapy-resistant acute myeloid leukemia" refers to a form of acute myeloid leukemia that is resistant or refractory to standard chemotherapy for acute myeloid leukemia. In one embodiment, the standard chemotherapy for acute myeloid leukemia comprises one or more approved chemotherapeutic agents selected from cytarabine, doxorubicin, daunorubicin (daunomycin), idarubicin, clardribine (Leustatin®, 2-CdA), fludarabine (Fludara®), topotecan, etoposide (VP-16), 6-thioguanine or 6-TG, hydroxyurea (Hydrea®), corticosteroids (e.g., prednisone or dexamethasone (Decadron®), methotrexate or MTX, 6-mercaptopurine or 6-MP, azacitidine (Vidaza®), decitabine (Dacogen®).

As used herein, "cytarabine-resistant acute myeloid leukemia" refers to a form of acute myeloid leukemia that is resistant or refractory to treatment of the disease with cytarabine, alone or in combination with one or more additional therapeutic agents.

As used herein, "double hit diffuse large B cell lymphoma" refers to a form of lymphoma or diffuse large B cell lymphoma where the lymphoma cells are altered at two oncogenes which are c-MYC and BCL2 or BCL6. In one embodiment, double hit diffuse large B cell lymphoma is treated in the method, and is characterized by gene alterations at c-MYC and BCL2. In another embodiment, double hit diffuse large B cell lymphoma is treated in the method, and is characterized by gene alterations at c-MYC and BCL6.

As used herein, "triple hit diffuse large B cell lymphoma" refers to a form of lymphoma or diffuse large B cell lymphoma where the lymphoma cells are altered at three oncogenes which are c-MYC, BCL2 and BCL6. In one embodiment, triple hit diffuse large B cell lymphoma is treated in the method.

In accordance with the present invention, the compound used in the method of treatment is represented by formula (I):

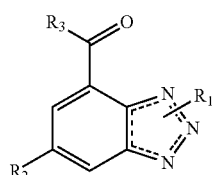
(I)

or a pharmaceutically acceptable salt, wherein the dotted lines [ . . . ] in the ring represent an optional bond which is present in any stable combination $R_1$ is selected from hydrogen and alkyl; $R_2$ is -A-$R_4$; A is arylene or tetrasubstituted arylene; wherein the substituent is halogen; $R_3$ is selected from hydroxy and amino; $R_4$ is selected from an aryl and a heteroaryl that is optionally substituted with one or more $R_5$; and $R_5$ is selected from alkyl and —$(CH_2)_n N(R_a)R_b$. $R_a$ and $R_b$ are independently selected from hydrogen, alkyl and —C(O)alkyl; alternatively $R_a$ and $R_b$ can be taken together with the nitrogen atom to which they are attached to form a 4-6 membered heterocyclyl containing 0-2 additional heteroatoms independently selected from O and N and is optionally substituted with alkyl. n is an integer selected from 0 and 1.

The compound represented by formula (I) described herein includes a regioisomer having any one of the following structures:

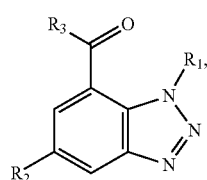
Regioisomer-1

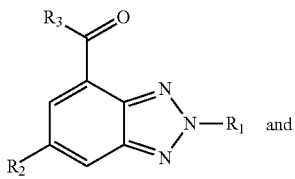
Regioisomer-2

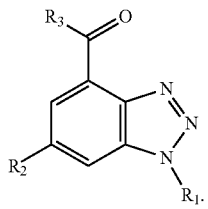
Regisisomer-3

Since the pharmaceutical activity of the regioisomers may differ, it may be desirable to use a specific regioisomer or a mixture of regioisomers. In such cases, a regioisomer can be separated at any of the possible stage either as an intermediate or as an end product by one or more processes well known to the person skilled in the art or even employed as such in the synthesis.

According to one embodiment, provided is a compound represented by formula (I), or a pharmaceutically acceptable salt thereof, in which $R_1$ is alkyl; in particular alkyl is methyl.

According to another embodiment, provided is a compound represented by formula (I), in which $R_2$ is -A-$R_4$; in which -A- is selected from arylene and tetrasubstituted arylene.

According to another embodiment, provided is a compound represented by formula (I), or a pharmaceutically acceptable salt thereof, in which $R_2$ is selected from

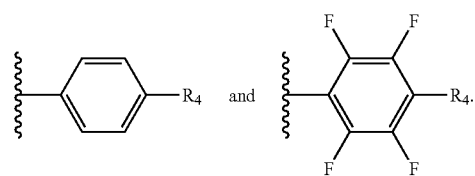

According to another embodiment, provided is a compound represented by formula (I), or a pharmaceutically acceptable salt thereof, in which $R_4$ is selected from optionally substituted phenyl; in which optional substituents are selected from methyl, acetylamino, isopropylaminomethyl, methylaminomethyl, dimethylaminomethyl,

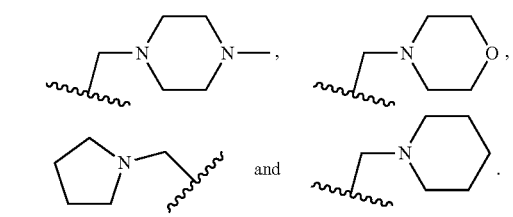

According to another embodiment, provided is a compound represented by formula (I), or a pharmaceutically acceptable salt thereof, in which $R_4$ is selected from 2,5-dimethyl-1H-pyrrole.

According to another embodiment, provided is a compound represented by formula (I), or a pharmaceutically acceptable salt thereof, in which $R_3$ is —OH and —NH$_2$.

According to yet another particular embodiment, a compound of the present invention is a compound represented by formula (Ia):

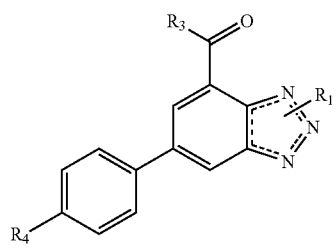

(Ia)

or a pharmaceutically acceptable salt thereof, wherein the dotted line [ - - - ], $R_1$, $R_3$ and $R_4$ are same as defined for formula (I).

According to yet another particular embodiment, a compound of the present invention is a compound represented by formula (Ib):

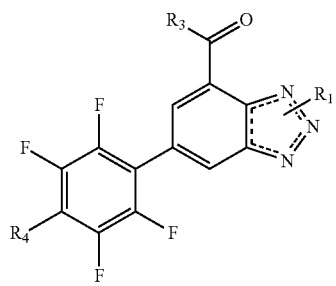

(Ib)

or a pharmaceutically acceptable salt thereof, wherein the dotted line [ - - - ], $R_1$, $R_3$ and $R_4$ are same as described in formula (I).

Examples of compounds that can be used in the disclosed treatment methods include:

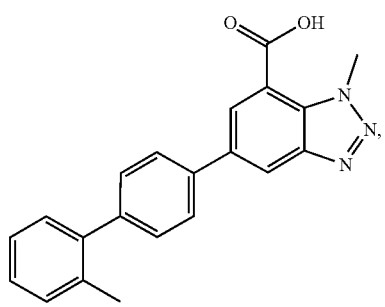

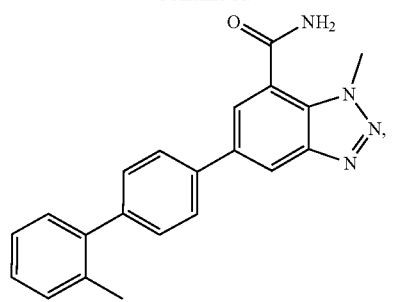

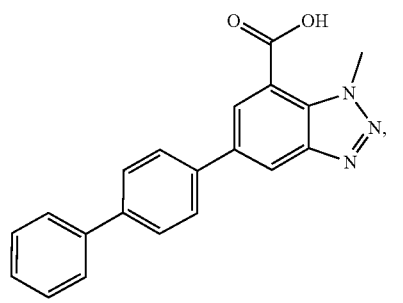

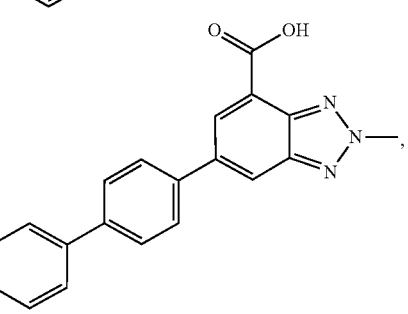

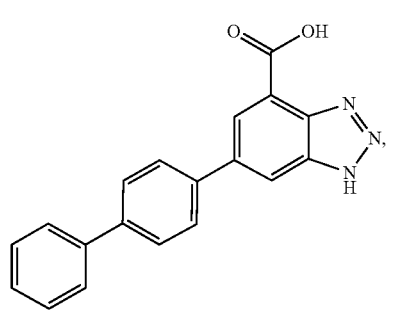

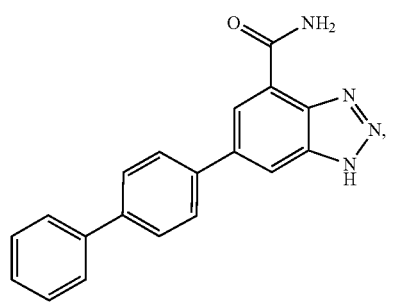

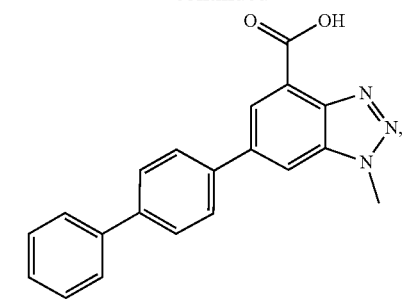
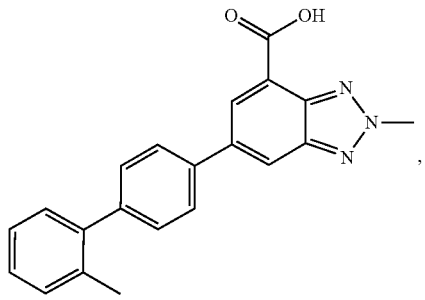
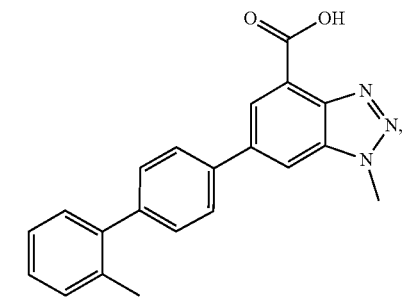
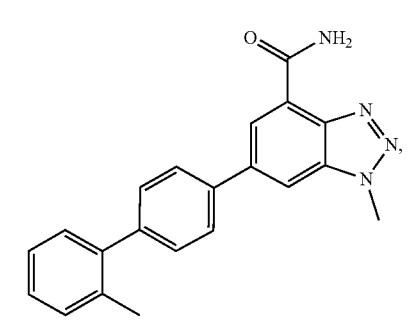
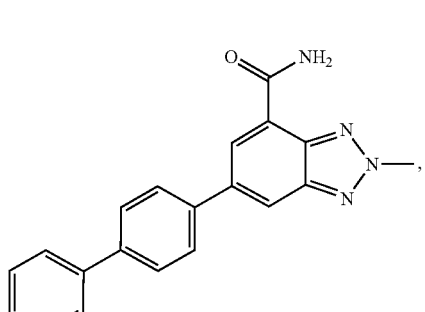
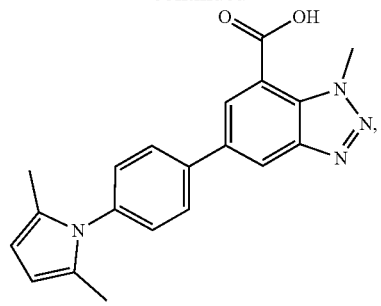
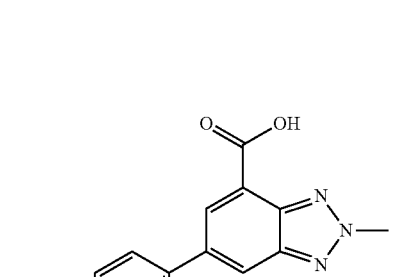
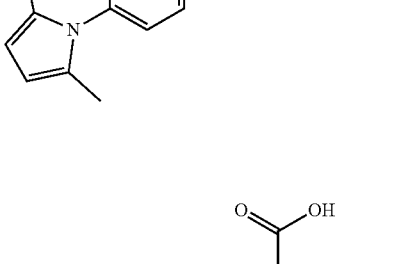
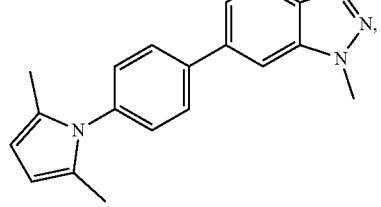
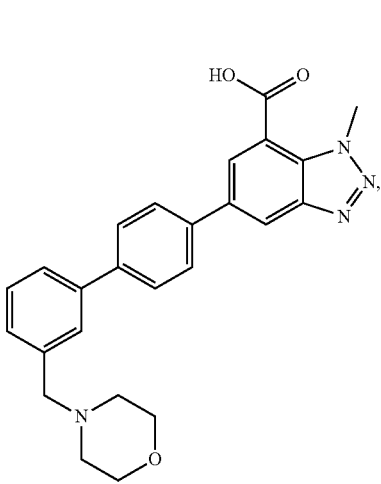

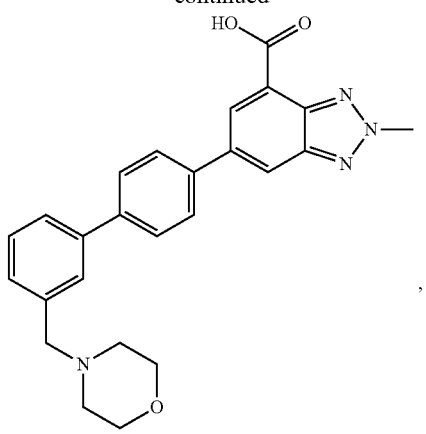
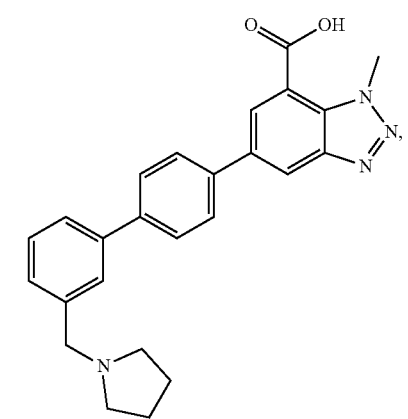
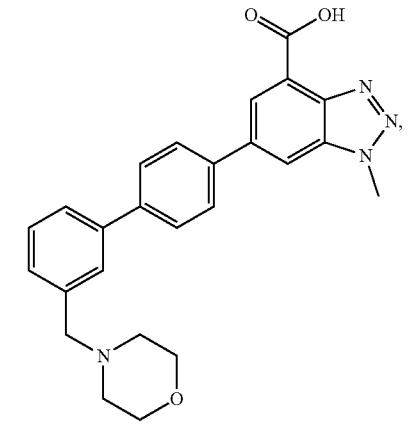
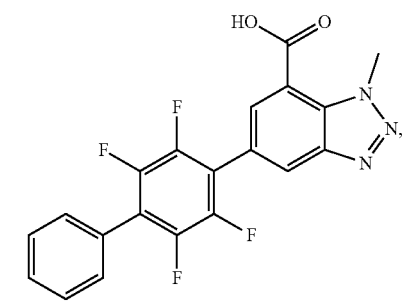
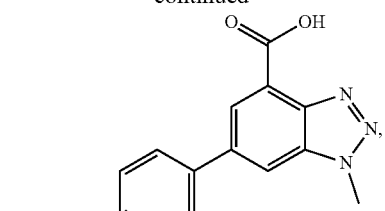
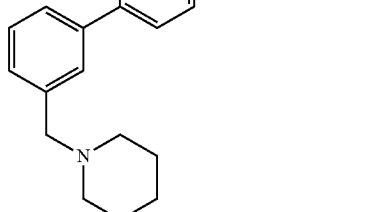
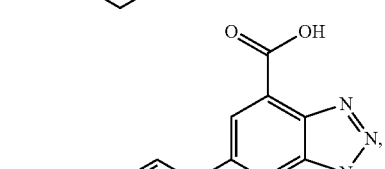
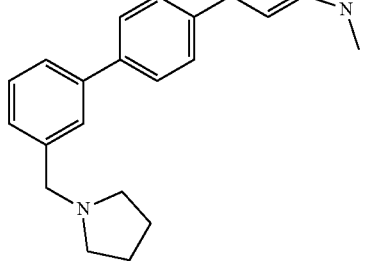
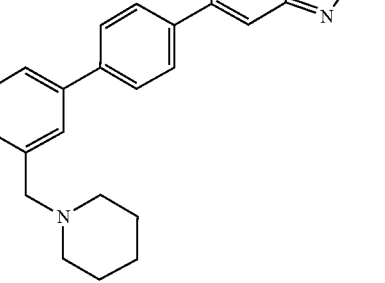

-continued
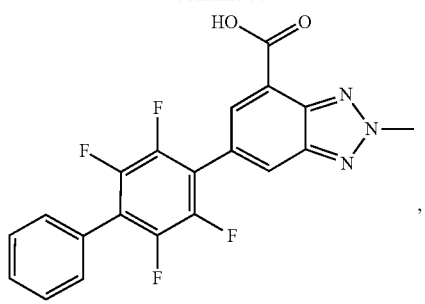
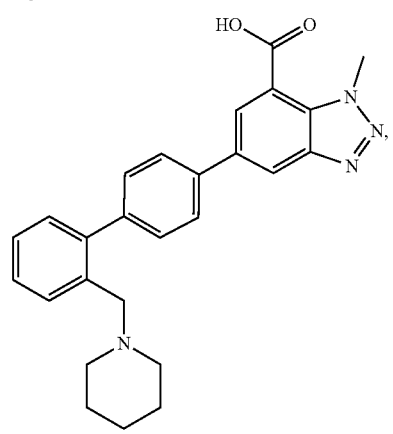
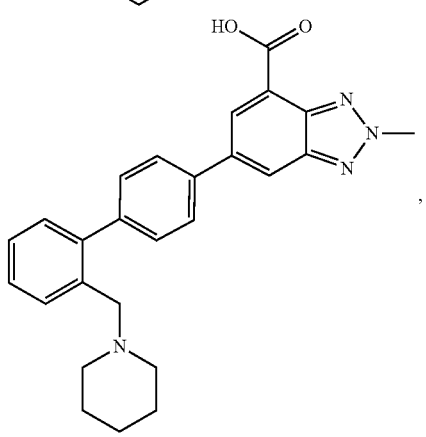
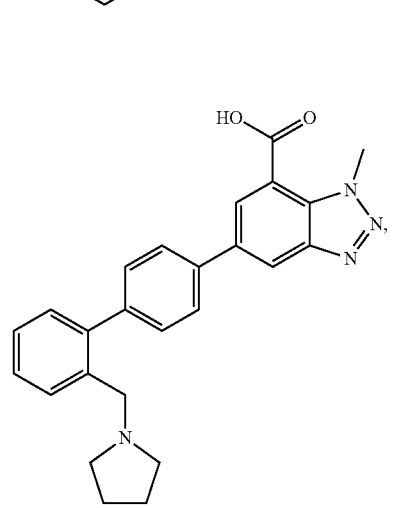
-continued
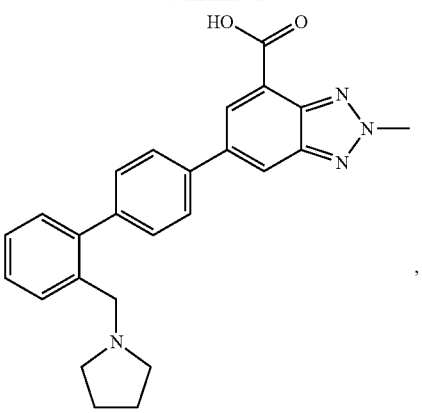
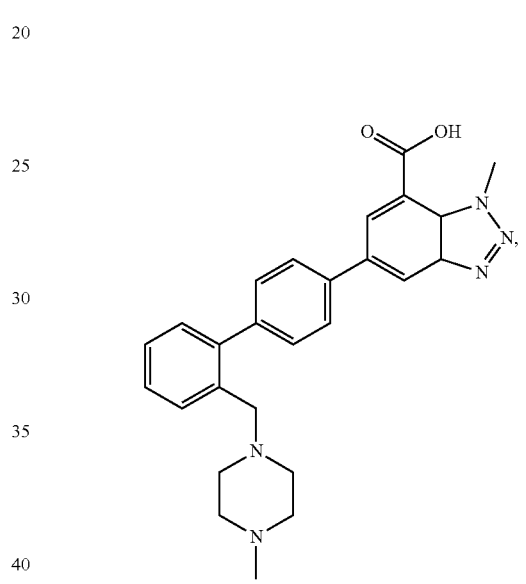
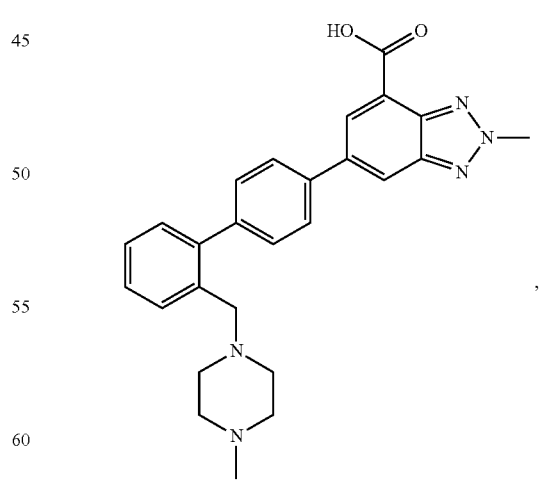

-continued
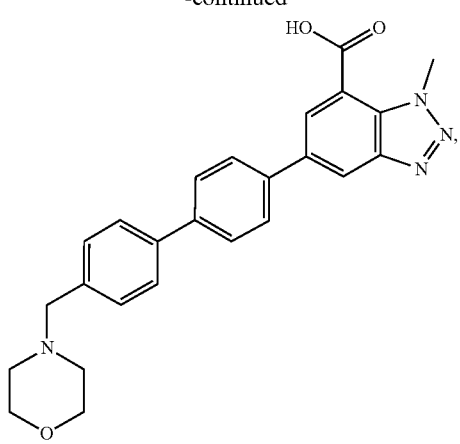
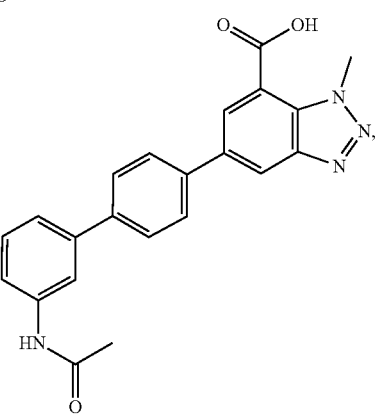
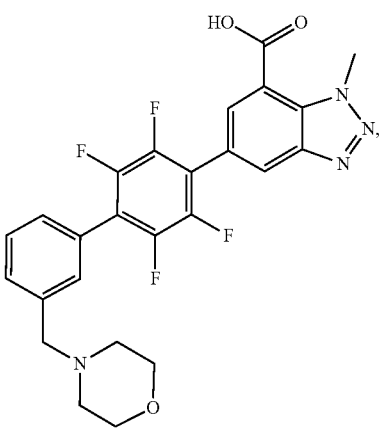
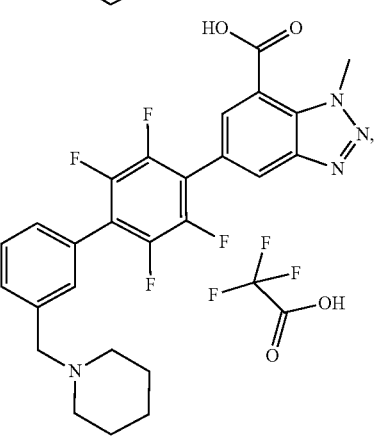
-continued
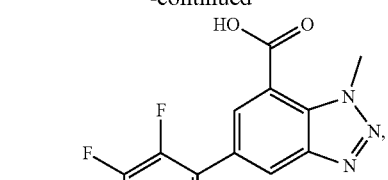
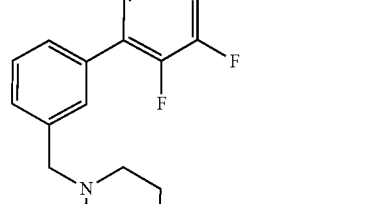
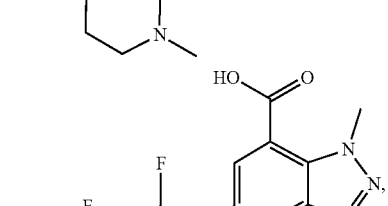
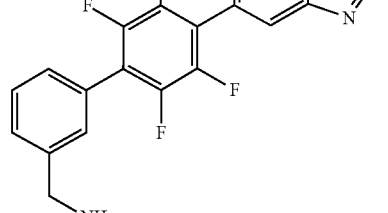
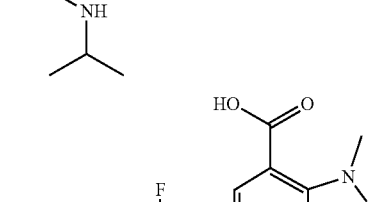
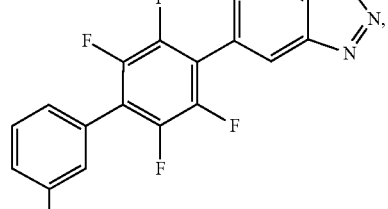
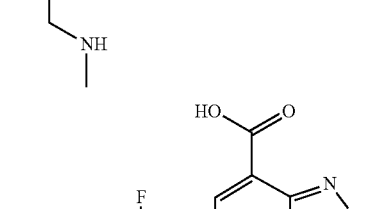
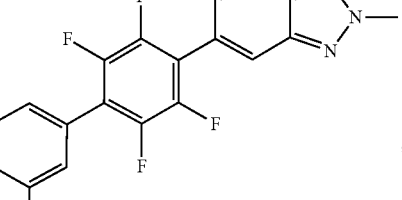
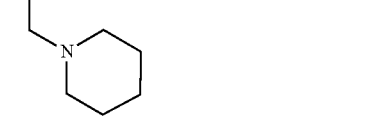

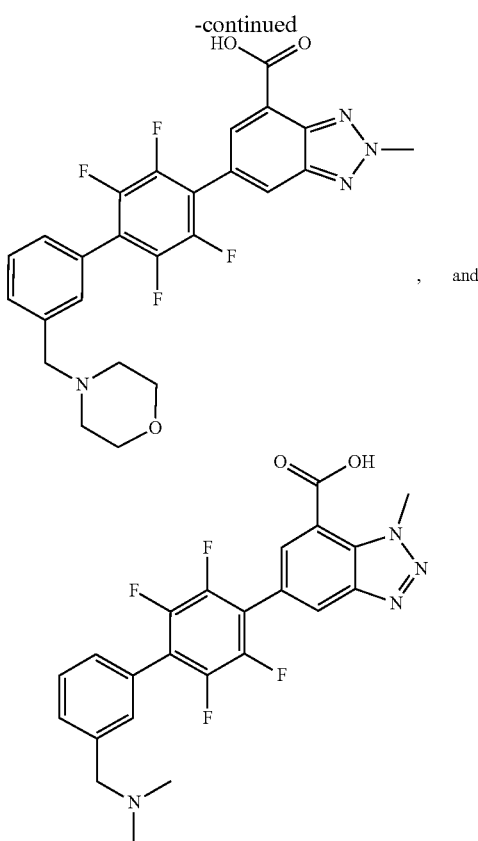

, and or a pharmaceutically acceptable salt thereof.

As used herein, "alkyl" refers to a hydrocarbon chain that may be a linear or branched chain, containing the indicated number of carbon atoms, for example, a $C_1$-$C_6$ alkyl group may have from 1 to 6 (inclusive) carbon atoms in it. Examples of $C_1$-$C_4$ and $C_1$-$C_6$ alkyl groups include, but are not limited to, methyl, ethyl, propyl, butyl, pentyl, hexyl, isopropyl, isobutyl, sec-butyl, tert-butyl, isopentyl, neopentyl, and isohexyl. An alkyl group can be unsubstituted or substituted with one or more suitable groups.

As used herein, "amino" refers to an —N— group, the nitrogen atom of said group being attached to a hydrogen, alkyl, cycloalkyl, aryl, heterocyclyl or any suitable groups. Representative examples of an amino group include, but are not limited to —$NH_2$, —$NHCH_3$ and —NH-cyclopropyl. An amino group can be unsubstituted or substituted with one or more of the suitable groups.

As used herein, "aryl" refers to an optionally substituted monocylic, bicyclic or polycyclic aromatic carbocyclic ring system of about 6 to 14 carbon atoms. Examples of a $C_6$-$C_{14}$ aryl group include, but are not limited to phenyl, naphthyl, biphenyl, anthryl, tetrahydronaphthyl, fluorenyl, indanyl, biphenylenyl, and acenaphthyl. Aryl group which can be unsubstituted or substituted with one or more suitable groups.

As used herein, "arylene" denotes a divalent monocyclic or bicyclic, saturated, unsaturated or aromatic carbocyclic ring having 6 to 14 carbon atoms which may be unsubstituted or substituted with one or more suitable groups.

As used herein, "halogen" or "halo" includes fluorine, chlorine, bromine or iodine.

As used herein, "hydroxy" refers to —OH group.

As used herein, "heterocyclyl" includes the definitions of "heterocycloalkyl" and "heteroaryl". The term "heterocycloalkyl" refers to a non-aromatic, saturated or partially saturated, monocyclic or polycyclic ring system of 3 to 10 member having at least one heteroatom or heterogroup selected from O, N, S, S(O), S(O)$_2$, NH and C(O). Exemplary heterocycloalkyl groups include piperdinyl, piperazinyl, morpholinyl, thiomorpholinyl, 1,3-dioxolanyl, 1,4-dioxanyl and the like. A heterocycloalkyl group can be unsubstituted or substituted with one or more suitable groups.

As used herein, "heteroaryl" refers to an unsaturated, monocyclic, bicyclic, or polycyclic aromatic ring system containing at least one heteroatom selected from oxygen, sulphur and nitrogen. Examples of $C_5$-$C_{10}$ heteroaryl groups include furan, thiophene, indole, azaindole, oxazole, thiazole, thiadiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, benzoxazole, benzothiazole, benzofuran, benzisoxazole, benzimidazole, N-methylbenzimidazole, azabenzimidazole, indazole, quinazoline, quinoline, and isoquinoline. Bicyclic heteroaryl groups include those where a phenyl, pyridine, pyrimidine or pyridazine ring is fused to a 5 or 6-membered monocyclic heterocyclyl ring having one or two nitrogen atoms in the ring, one nitrogen atom together with either one oxygen or one sulfur atom in the ring, or one O or S ring atom. A heteroaryl group can be unsubstituted or substituted with one or more suitable groups.

As used herein, "heteroatom" refers to a sulfur, nitrogen or oxygen atom.

"Optionally substituted or substituted" as used herein means that at least one hydrogen atom of the optionally substituted group has been substituted with suitable substitutions as exemplified but not limited to halogen, nitro, cyano, hydroxy, oxo (=O), thio (=S), —N($C_1$-$C_3$alkyl)C(O)($C_1$-$C_6$alkyl), —NHC(O)($C_1$-$C_6$alkyl), —NHC(O)(cycloalkyl), —NHC(O)(aryl), —NHC(O)(heterocyclyl), —NHC(O)(heteroaryl), —NHC(O)H, —C(O)$NH_2$, —C(O)NH($C_1$-$C_6$alkyl), —C(O)NH(cycloalkyl), —C(O)NH(heterocyclyl), —C(O)NH(heteroaryl), —C(O)N($C_1$-$C_6$alkyl)($C_1$-$C_6$alkyl), —S(O)NH($C_1$-$C_6$alkyl), —S(O)$_2$NH($C_1$-$C_6$alkyl), —S(O)NH(cycloalkyl), —S(O)$_2$NH(cycloalkyl), carboxy, —C(O)O($C_1$-$C_6$alkyl), —C(O)($C_1$-$C_6$alkyl), =N—OH, substituted or unsubstituted alkyl, substituted or unsubstituted haloalkyl, substituted or unsubstituted alkoxy, substituted or unsubstituted haloalkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted heteroaryl, substituted or unsubstituted heterocyclyl, substituted or unsubstituted heteroarylalkyl, substituted or unsubstituted heterocyclic ring.

As used herein, "pharmaceutically acceptable salt" is taken to mean an active ingredient, which comprises a compound of the formula (I) in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

As used herein, the term "subject" and "patient" may be used interchangeably, and means a mammal in need of treatment, e.g., companion animals (e.g., dogs, cats and the like), farm animals (e.g., cows, pigs, horses, sheep, goats and the like) and laboratory animals (e.g., rats, mice, guinea pigs and the like). Typically, the subject is a human in need of treatment.

As used herein, the term "treating" or 'treatment" refers to obtaining desired pharmacological and/or physiological effect. The effect can be therapeutic, which includes achieving, partially or substantially, one or more of the following results: partially or totally reducing the extent of the disease, disorder or syndrome; ameliorating or improving a clinical symptom or indicator associated with the disorder; and delaying, inhibiting or decreasing the likelihood of the progression of the disease, disorder or syndrome.

The term "a therapeutically effective amount" means an amount of the compound of formula (I), or a pharmaceutically acceptable salt thereof, e.g., 0.1 mg to 1000 mg/kg body weight, when administered to a subject, which results in beneficial or desired results, including clinical results, i.e., reversing, alleviating, inhibiting, reducing or slowing the progression of a disease or condition treatable by a compound of formula (I), or a pharmaceutically acceptable salt thereof, reducing the likelihood of recurrence of a disease or condition treatable by a compound of formula (I), or a pharmaceutically acceptable salt thereof or one or more symptoms thereof, e.g., as determined by clinical symptoms, compared to a control. The expression "therapeutically effective amount" also encompasses the amounts which are effective for increasing normal physiological function.

The term "pharmaceutically acceptable carrier" or "pharmaceutically acceptable excipient" refers to a non-toxic carrier, diluent, adjuvant, vehicle or excipient that does not adversely affect the pharmacological activity of the compound with which it is formulated, and which is also safe for human use. Pharmaceutically acceptable carriers that may be used in the compositions of this disclosure include, but are not limited to, ion exchangers, alumina, aluminum stearate, magnesium stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances (e.g., microcrystalline cellulose, hydroxypropyl methylcellulose, lactose monohydrate, sodium lauryl sulfate, and crosscarmellose sodium), polyethylene glycol, sodium carboxymethylcellulo se, polyacrylates, waxes, polyethylene-polyoxypropylene-block polymers, polyethylene glycol and wool fat.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

For example, in the case of oral administration as tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form can be added to the powder mixture before the filling operation. A disintegrant or solubiliser, such as, for example, agar-agar, calcium carbonate or sodium carbonate, may likewise be added in order to improve the availability of the medica-ment after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbant, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tableting machine, giving lumps of non-uniform shape which are broken up to form granules. The granules can be lubricated by addition of stearic acid, a stearate salt, talc or mineral oil in order to prevent sticking to the tablet casting moulds. The lubricated mixture is then pressed to give tablets. The active ingredients can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compounds. Syrups can be prepared by dissolving the compounds in an aqueous solution with a suitable flavour, while elixirs are prepared using a non-toxic alcoholic vehicle. Suspensions can be for-mulated by dispersion of the compounds in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be encapsulated in microcapsules. The formulation can also be prepared in such a way that the release is extended or retarded, such as, for example, by coating or embedding of particulate material in polymers, wax and the like.

Compounds represented by formula (I) or a pharmaceutically acceptable salt thereof may be prepared using the methods and procedures described in U.S. Pat. No. 9,630,932, which is incorporated herein by reference in its entirety.

Although the invention is illustrated by certain of the following examples, it is not to be construed as being limited thereby; but rather, the invention encompasses the generic area as hereinbefore disclosed. Various modifications and embodiments can be made without departing from the spirit and scope thereof.

EXAMPLES

Example 1

In Vitro Growth Inhibition of Multiple Human Cancer Cell Lines by Compound 1

A tumor cell line panel screen aimed at identifying tumor cell subsets that were particularly sensitive to inhibition of DHODH with Compound 1 was performed. Compound 1 is represented by the following structural formula:

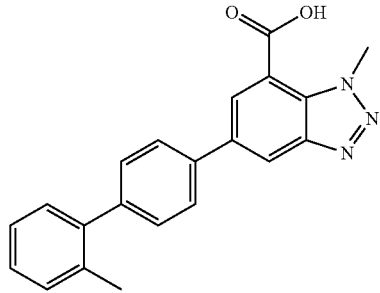 [SMILES: Cc1ccccc1-c1ccc(-c2cc(C(=O)O)c3c(c2)nnn3C)cc1]

These cell lines were treated with Compound 1 for a total of 72 hrs.

Assessment of tumor growth rates after the 72-hour treatment, as shown in FIG. 1 and Table 1, revealed that a distinct subset of cell lines (depicted by grey dots in FIG. 1) were sensitive to Compound 1. The majority of the cell lines exhibiting high sensitivity to Compound 1 are of hematopoietic origin though some solid tumor lines also exhibited high sensitivity (Table 1). For purposes of generating FIG. 1, sensitive cell lines were defined as exhibiting ≥75% maximal growth inhibition and a log $GI_{50}$ value of <1.5 μM. In Table 1, a maximum inhibition of 100 represents complete growth inhibition; a max inhibition value>100 represents cell killing.

Figure 2:
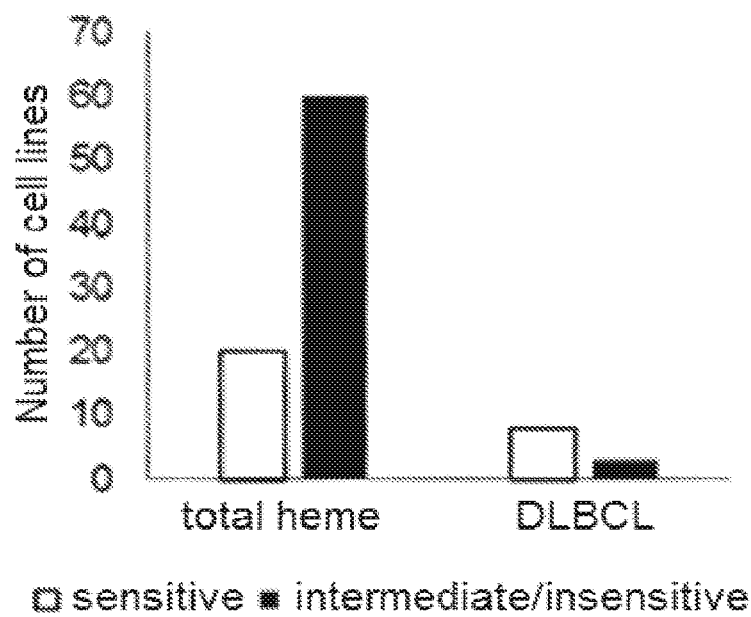
FIG. 2 shows the sensitivity of an additional panel of human cancer lines of heme lineage towards growth inhibition by Compound 1 of the invention.
Figure 3:
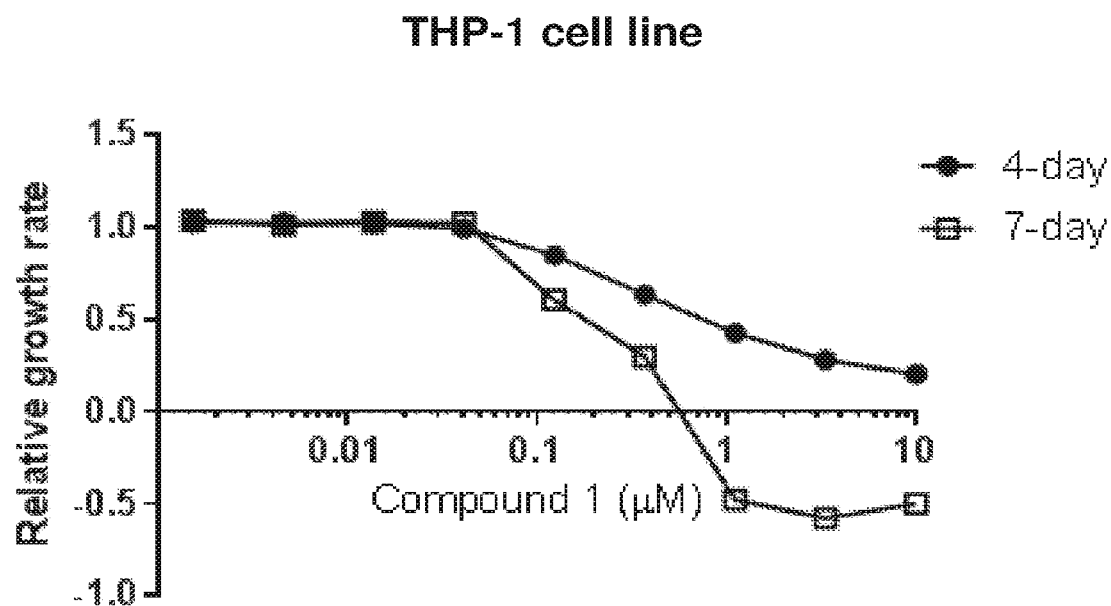
FIG. 3 shows the 4-day and 7-day relative growth curves of the THP-1 cell line treated with Compound 1.
Figure 4:
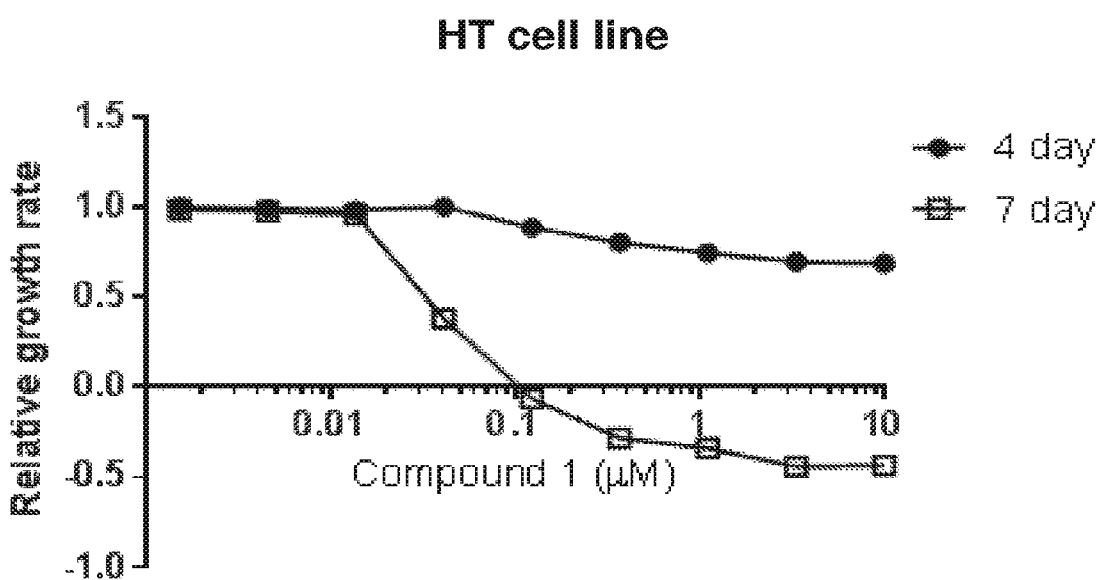
FIG. 4 shows the 4-day and 7-day relative growth curves of the HT cell line treated with Compound 1.

A follow-up screen was performed on an expanded panel of cell lines of heme lineage in a 4-day growth assay. Growth was assessed by Cell-Titer Glo measurements on day 0 and day 4. As shown in FIG. 2, 25% of the heme lines screened (20/80) exhibited sensitivity to Compound 1. A subset of the heme lines that were of intermediate sensitivity (defined as >50% and <75% growth rate inhibition) or insensitive (defined as <50% growth rate inhibition) to Compound 1 in this follow-up screen were subjected to extended growth assays to evaluate if increased treatment time modulated their sensitivity profile. Specifically, these heme lines were pretreated with Compound 1 for three days at the indicated concentrations and then re-plated for a standard 4-day growth assay in fresh media/drug. The vast majority of re-tested heme lines exhibited strong sensitivity to Compound 1 following 7 days of treatment (Table 2. FIGS. 3 and 4 show 4-day and 7-day relative growth curves of THP-1 and HT cell lines treated with Compound 1, respectively. Growth rates were calculated using the formula: $\ln(T_{96}/T_0)$/time (hrs) and plotted relative to DMSO treated cells. The strong sensitivity of THP-1 cells to Compound 1 in this assay is of particular interest given their resistance to the AML standard of care drug cytarabine (Ara-C), reportedly due to high expression of SAMHD1, which inactivates the active metabolite Ara-CTP. In other words, THP-1 cells highly express SAMHD1, which correlates to a mechanism of resistance to cytarabine (Schneider et al., *Nature Medicine*, 2017, 23(2), 250-254; Herold et al., *Cell Cycle*, 2017, 16(11):1029-1038). Yet, the cell line was shown to be sensitive to Compound 1 in the 7-day assay. Thus, Compound 1 may have particular benefit in treating AML patients that have developed resistance to standard chemotherapeutic agents.

TABLE 1

$GI_{50}$ and maximum growth inhibition of various cell lines treated with Compound 1.

| Cell line | Primary site | Disease | $GI_{50}$ (μM) | Maximum growth inhibition |
|---|---|---|---|---|
| SNU478 | Biliary tract | Biliary cancer or cancer of the ampulla of Vater | 0.05 | 75.4 |
| NCIH460 | Lung | Non-small cell lung cancer/carcinoma | 0.07 | 96.6 |
| NCIH1155 | Lung | Non-small cell lung cancer/carcinoma | 0.11 | 171.4 |
| NCIH1666 | Lung | Non-small cell lung cancer/carcinoma | 0.13 | 118.7 |
| BICR22 | Upper aero-digestive tract | Cancer of the upper aerodigestive tract (tongue) | 0.21 | 78.9 |
| HLF | Liver | Liver cancer (hepatocellular carcinoma) | 0.36 | 85.8 |
| LCLC103H | Lung | Non-small cell lung cancer/carcinoma | 0.64 | 87.8 |
| NCIH1581 | Lung | Non-small cell lung cancer/carcinoma | 1.13 | 94.4 |
| NCIH1435 | Lung | Non-small cell lung cancer/carcinoma | 1.25 | 117.0 |
| OAW42 | Ovary | Cancer of the ovary | 1.31 | 77.6 |

TABLE 2

4-day and 7-day sensitivity of various heme cell lines treated with Compound 1.

| Cell line | Disease | Sensitivity 4-day | 7-day |
|---|---|---|---|
| NALM-1 | Chronic myeloid leukemia (chronic monocytic leukemia) | ** | *** |
| HT | B-cell lymphoma/Diffuse mixed cell lymphoma | * | *** |
| F36P | Acute myeloid leukemia (secondary to myelodysplastic syndrome) | ** | *** |
| THP-1 | Acute myeloid leukemia/ Acute monocytic leukemia | ** | *** |
| AML-193 | Acute myeloid leukemia/ Acute monocytic leukemia | ** | *** |
| NALM-16 | Acute lymphoblastic leukemia (childhood B acute lymphoblastic leukemia) | ** | *** |
| BCP-1 | B-cell lymphoma/Primary effusion lymphoma | * | *** |
| TF1 | Acute myeloid leukemia/ Erythroleukemia | * | *** |
| HEL | Acute myeloid leukemia/ Erythroleukemia | ** | *** |

\* insensitive
\*\* intermediate
\*\*\* sensitive

Example 2

Figure 5A:
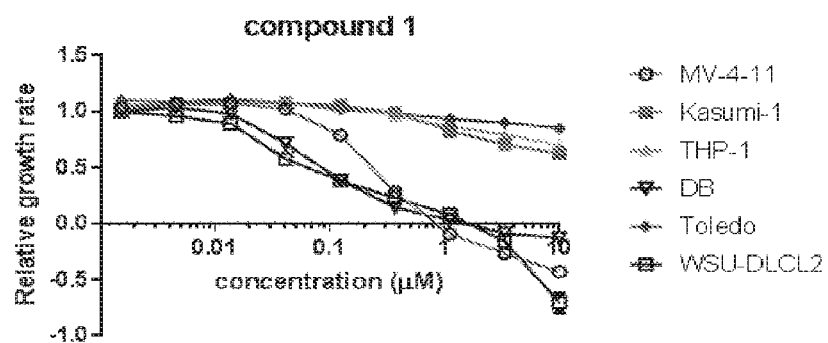
FIG. 5A shows the relative growth rate vs. concentration sensitivity profiles of MV411, Kasumi-1, THP-1, DB, Toledo and WSU-DLCL2 cell lines towards varying concentrations of Compound 1.
Figure 5B:
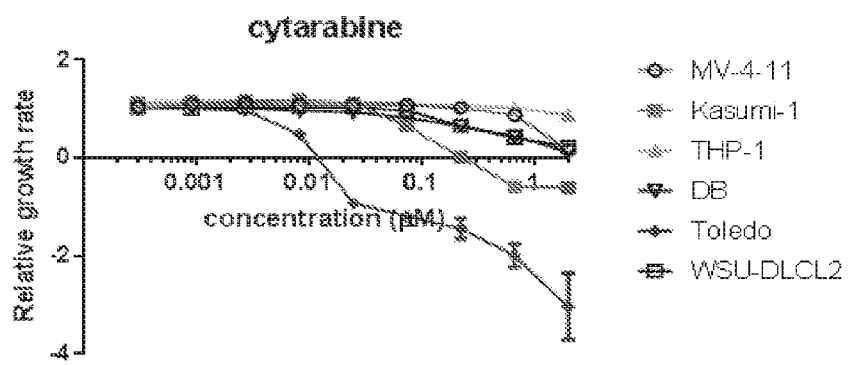
FIG. 5B shows the relative growth rate vs. concentration sensitivity profiles of MV411, Kasumi-1, THP-1, DB, Toledo and WSU-DLCL2 cell lines towards varying concentrations of cytarabine.
Figure 5C:
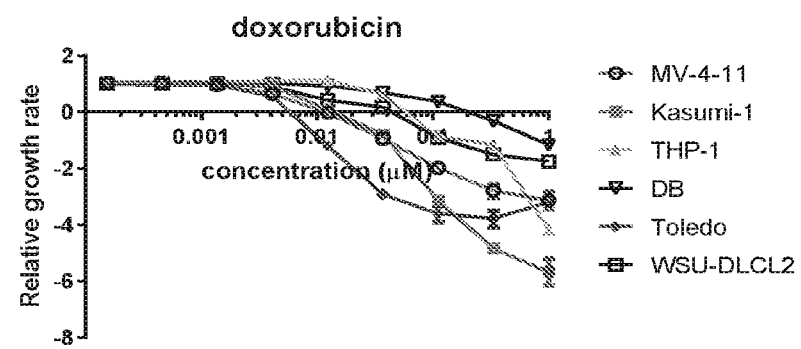
FIG. 5C shows the relative growth rate vs. concentration sensitivity profiles of MV411, Kasumi-1, THP-1, DB, Toledo and WSU-DLCL2 cell lines towards varying concentrations of doxorubicin.

Comparison of Compound 1 Sensitivity Profiles Against Cytarabine and Doxorubicin Sensitivity Profiles The sensitivity profile of Compound 1 against a subset of heme lines was compared to the sensitivity profiles other agents that are used as standard of care (SOC) in heme malignancies. Compound 1 displayed a sensitivity profile (FIG. 5A) distinct from cytarabine (FIG. 5B) and doxorubicin (FIG. 5C) sensitivity profiles, thereby suggesting that the mechanism of action of Compound 1 is different from those of cytarabine and doxorubicin.

Example 3

In Vitro Growth Inhibition of Double Hit Diffuse Large B Cell Lymphoma Human Cancer Cell Lines by Compound 1

Figure 6:
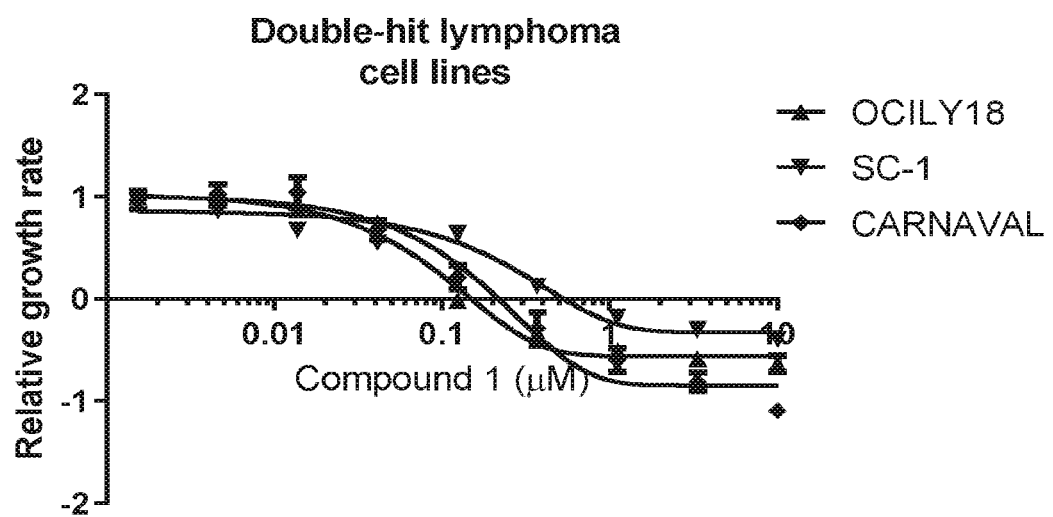
FIG. 6 is a curve showing the relative growth rate of OCILY18, SC-1 and CARNAVAL double hit diffuse large B cell lymphoma (DLBCL) cell lines treated with various concentrations of Compound 1 for 96 hours.

Three patient-derived DLBCL lymphoma cell lines classified as double-hit DLBCL, namely OCILY18, SC-1 and CARNAVAL, were found to be highly sensitive to inhibition by Compound 1 in a 96-hr growth assay (FIG. 6).

Example 4

Compound 1 Effectively Blocks Tumor Growth in Patient-Derived Double Hit DLBCL Xenograft Model A strong block in in vivo tumor growth was observed with Compound 1 in the OCILY-19 double hit diffuse large B-cell lymphoma (DLBCL) xenograft model. $7 \times 10^6$ OCTLY-19 cells were implanted subcutaneously into CB17 SCID mice. Mice (n=15-18/group) were treated with vehicle or Compound 1 at the indicated dose/frequency once tumors reached an average of ~150 mm$^3$. Tissues were collected at the indicated timepoints post-last dose for PK and biomarker analyses.

Figure 7A:
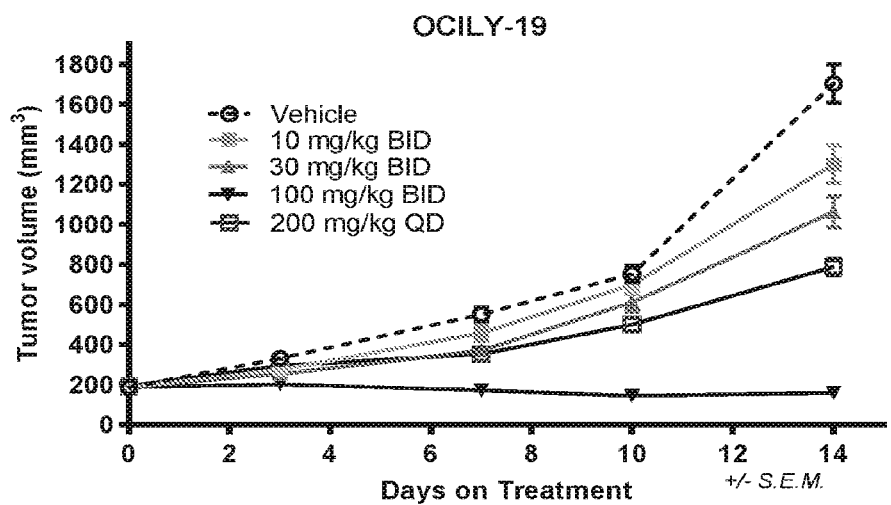
FIG. 7A shows OCILY-19 double hit diffuse large B cell lymphoma (DLBCL) tumor growth curves in CB17 SCID mice when left untreated (vehicle) or treated with 10 mg/kg of Compound 1, BID; 30 mg/kg of Compound 1, BID; 100 mg/kg of Compound 1, BID; and 200 mg/kg of Compound 1, QD, all measured over the course of 14 days.
Figure 7B:
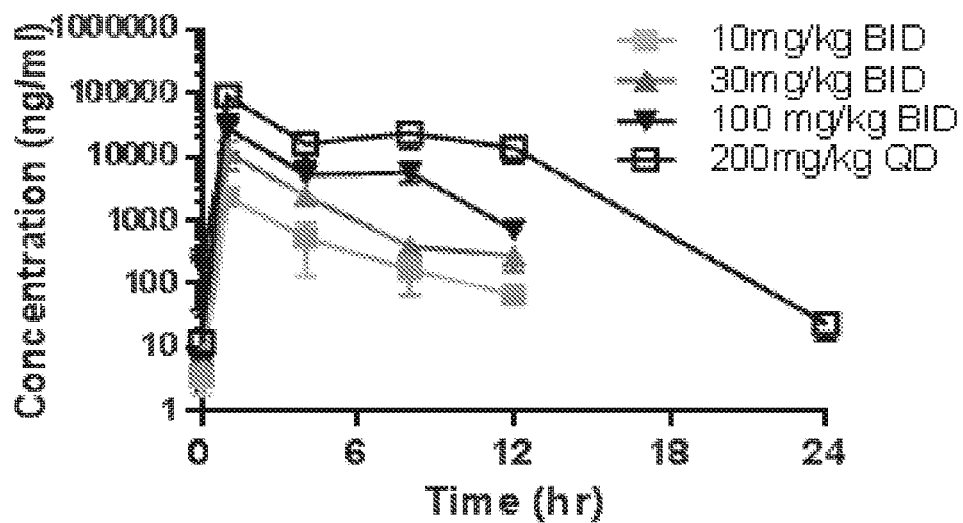
FIG. 7B shows the pharmacokinetic profiles of Compound 1, administered at the dosages described for FIG. 7A, in the plasma of the CB17 SCID mice, at the indicated timepoints following the last dose at end of study.
Figure 7C:
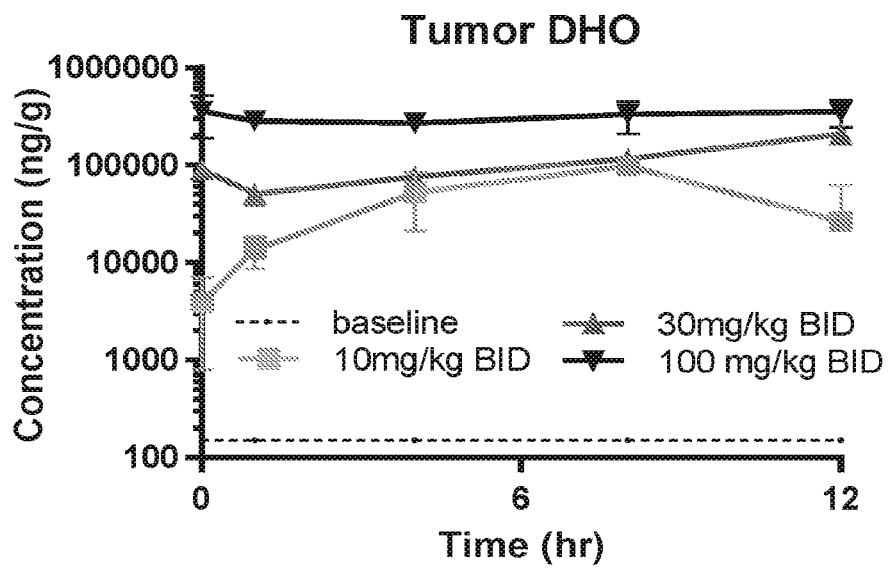
FIG. 7C shows the DHO levels in the untreated (vehicle) OCILY-19 tumors and tumors treated with compound 1 at the indicated doses, measured over the course of 12 hours following the last dose at end of study.
Figure 7D:
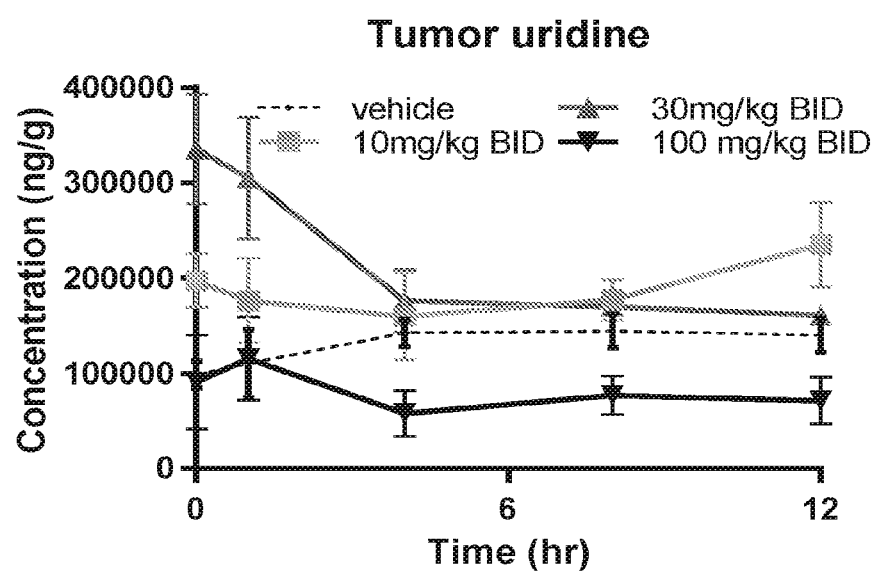
FIG. 7D shows the uridine levels in the untreated (vehicle) OCILY-19 tumors and tumors treated with compound 1 at the indicated doses, measured over the course of 12 hours following the last dose at end of study.

Degree of pathway modulation and tumor growth inhibition was demonstrated to be dose and schedule dependent (FIG. 7A). The 100 mg/kg BID dosing regimen resulted in superior efficacy compared to the 10 and 30 mg/kg BID dose arms and this correlated with a larger increase in tumor DHO (FIG. 7C) as well as a decrease in total tumor uridine pools (FIG. 7D). The 200 mg/kg QD regimen was less efficacious than the 100 mg/kg BID dosing regimen due to the short half-life of Compound 1 in mice, resulting in lower trough drug concentrations with QD dosing (see FIG. 7B).

Example 5

Compound 1 Effectively Blocks Tumor Growth in Patient-Derived Triple Hit DLBCL Xenograft Model Efficacy of Compound 1 in a triple hit DLBCL patient-derived xenograft model (DLBCL_1) was assessed as part of a larger screen for sensitivity in PDX models of hematologic origin. Tumor-bearing mice (n=3/group) were treated with vehicle or Compound 1 at 100 mg/kg BID PO.

Figure 8:
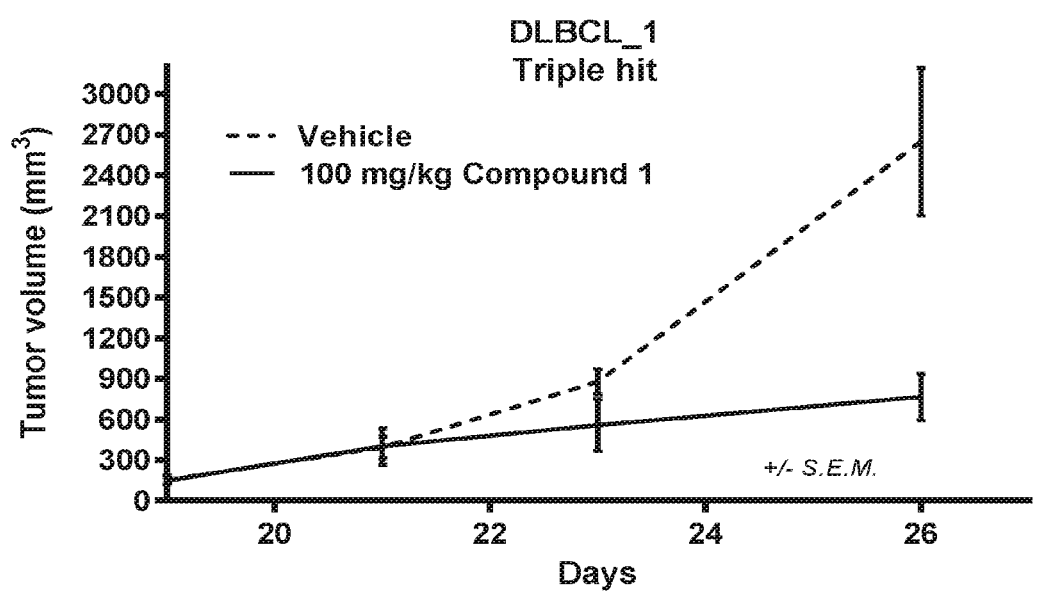
FIG. 8 shows patient-derived DLBCL_1 (triple hit DLBCL) tumor growth curves in CB17 SCID mice when left untreated (vehicle) or treated with 100 mg/kg of Compound 1, BID.

As shown in FIG. 8, anti-tumor activity of Compound 1 was observed in the DLBCL_1 model tested, with >70% TGI.

What is claimed is:

1. A method of treating double hit diffuse large B cell lymphoma or triple hit diffuse large B cell lymphoma in a subject, comprising administering to the subject a therapeutically effective amount of a compound represented by the following structural formula:

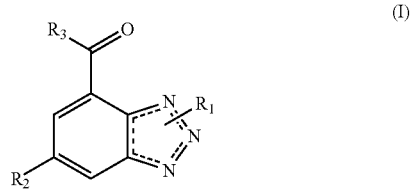

(I)

or a pharmaceutically acceptable salt thereof; wherein:

the dotted lines [ . . . ] in the ring represent an optional bond which may be present in any stable combination;

$R_1$ is selected from hydrogen and alkyl;

$R_2$ is -A-$R_4$;

A is arylene or tetrasubstituted arylene; wherein the substituent is halogen;

$R_3$ is selected from hydroxy and amino;

$R_4$ is selected from an aryl and a heteroaryl that is optionally substituted with one or more $R_5$;

$R_5$ is selected from alkyl and —$(CH_2)_n N(R_a)R_b$;

$R_a$ and $R_b$ are independently selected from hydrogen, alkyl and —C(O)alkyl;

alternatively $R_a$ and $R_b$ can be taken together with the nitrogen atom to which they are attached to form a 4-6 membered heterocyclyl containing 0-2 additional heteroatoms independently selected from O and N and is optionally substituted with alkyl; and n is an integer selected from 0 and 1.

2. The method according to claim 1, wherein the cancer is double hit diffuse large B cell lymphoma.

3. The method according to claim 1, wherein the cancer is triple hit diffuse large B cell lymphoma.

4. The method according to claim 1, wherein the compound is selected from:

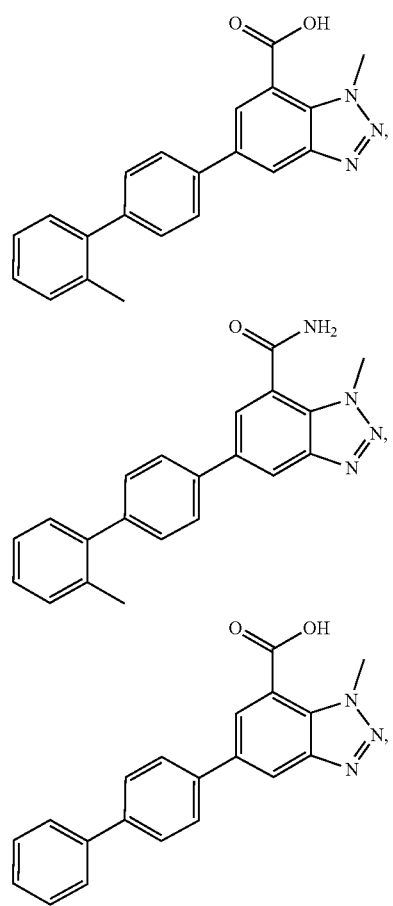
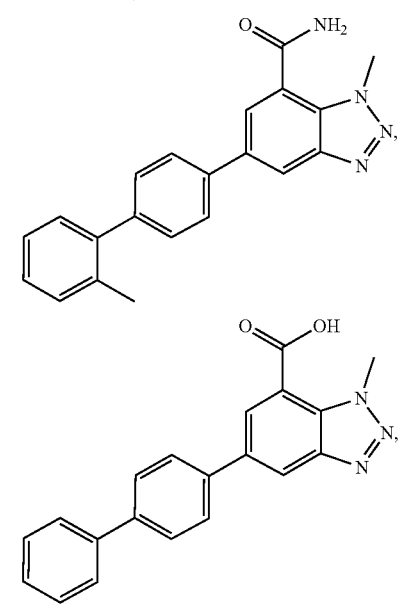
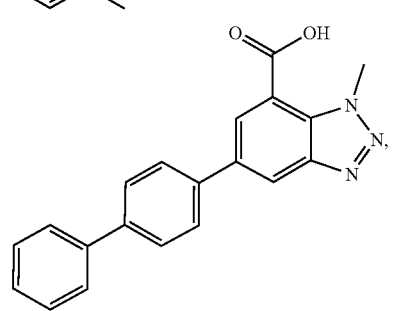
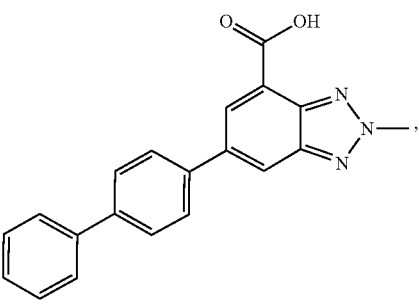
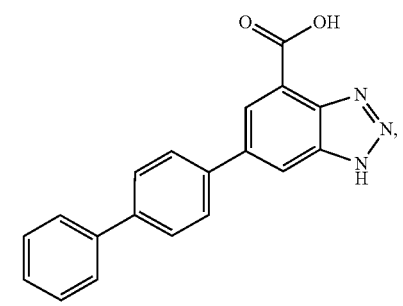
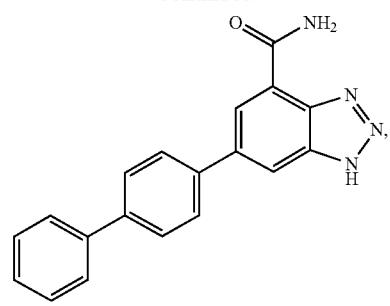
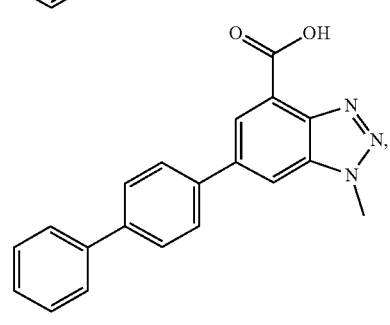
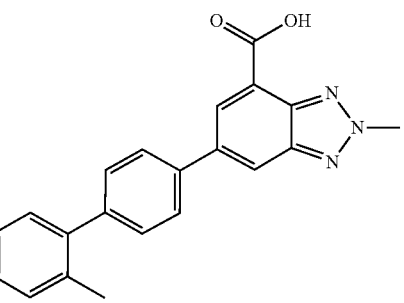
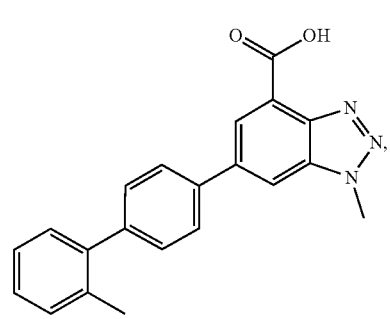
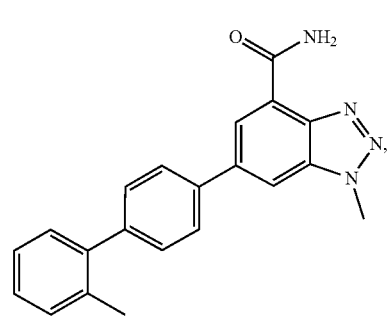

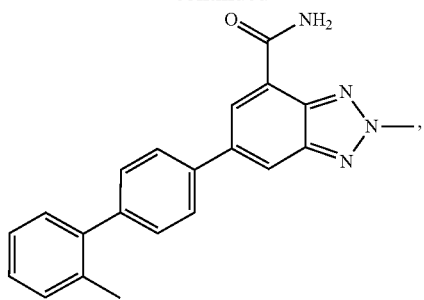
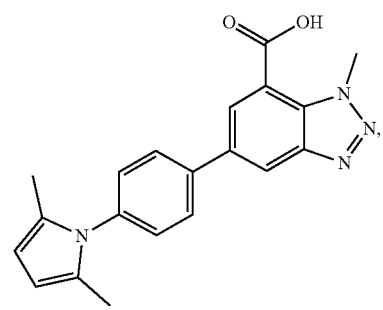
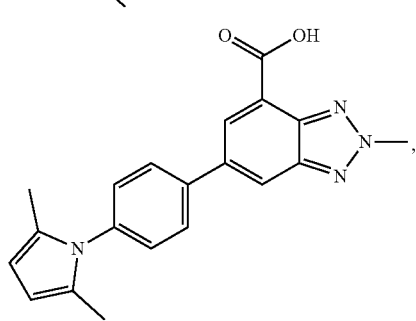
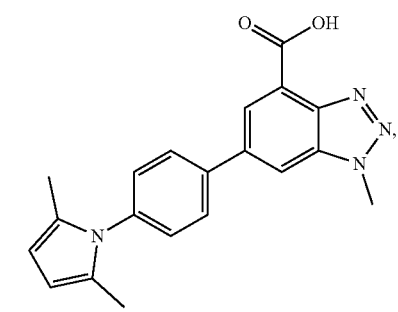
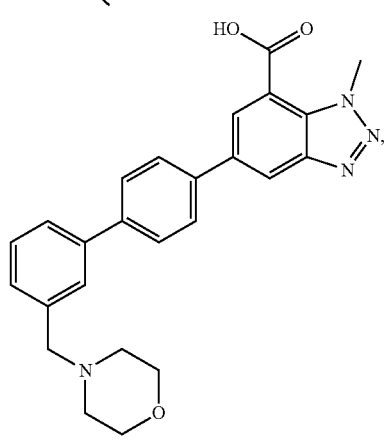
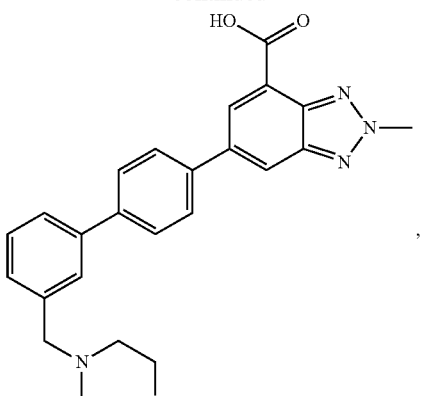
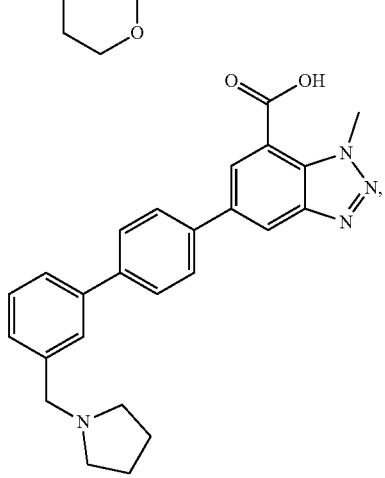
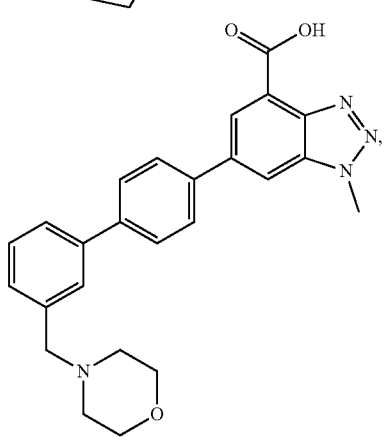
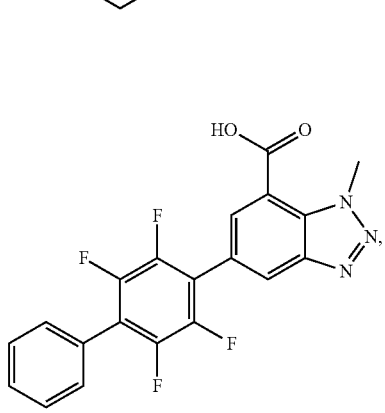

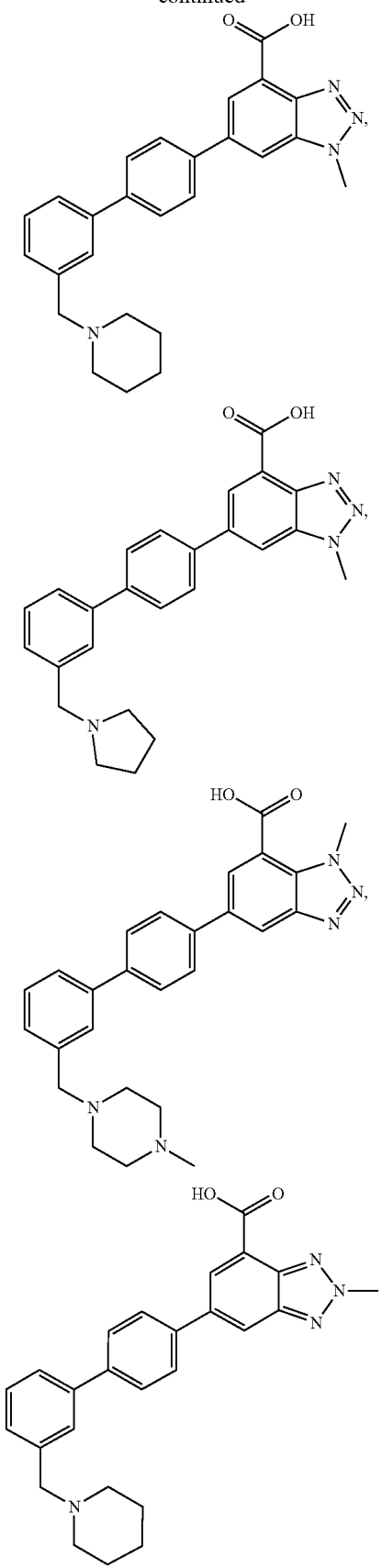
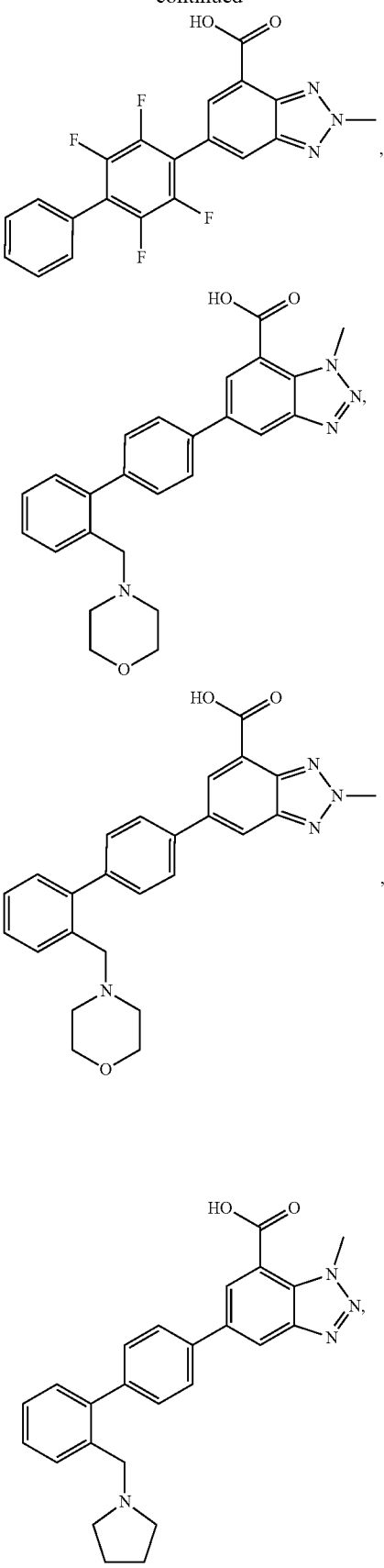

31
-continued
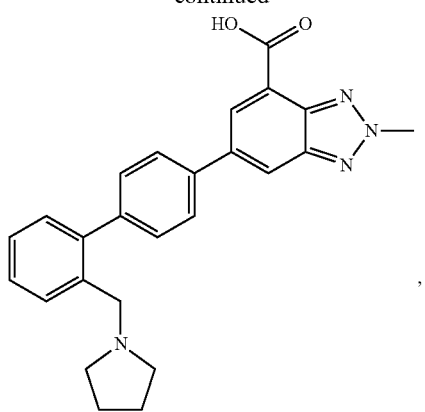
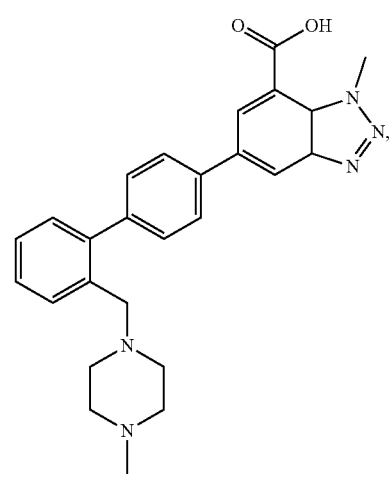
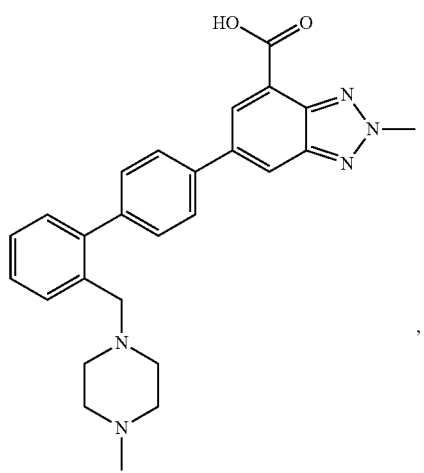
32
-continued
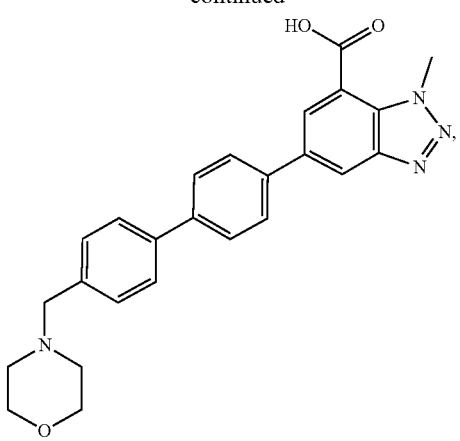
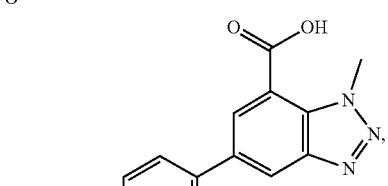
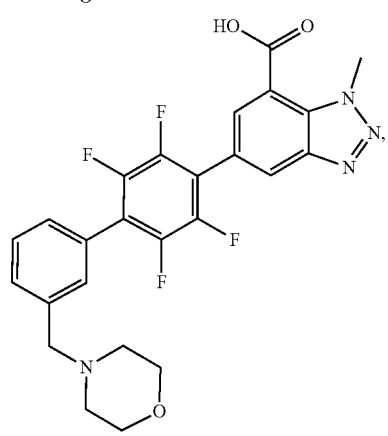
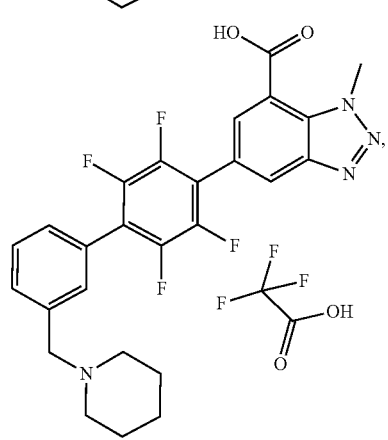

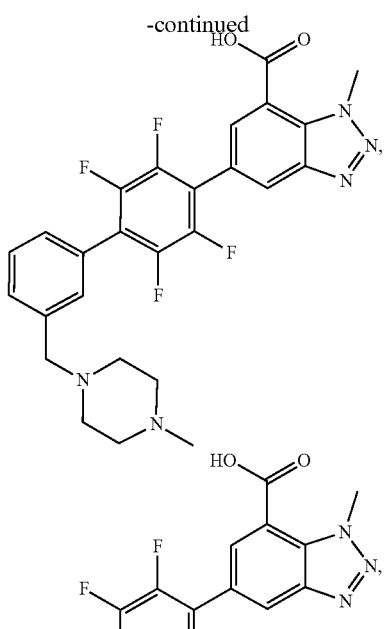
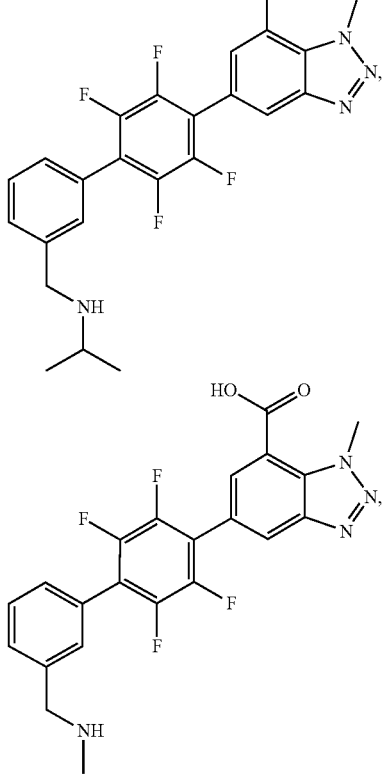
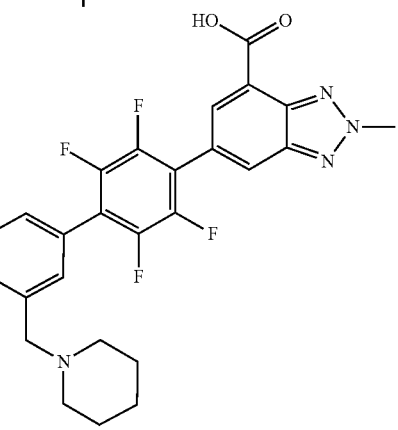
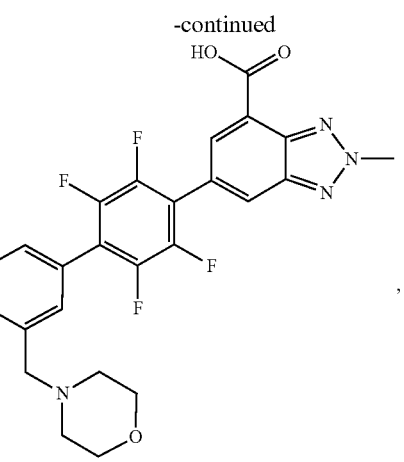
, and
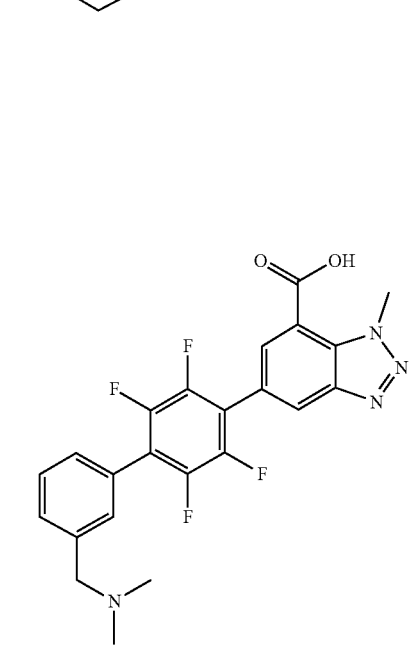
or a pharmaceutically acceptable salt thereof.
5. A method of treating double hit diffuse large B cell lymphoma, comprising administering to the subject a therapeutically effective amount of the compound:
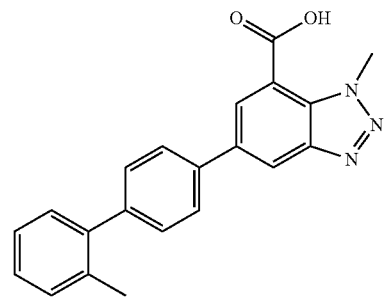 [SMILES: Cc1ccccc1-c1ccc(-c2cc(C(=O)O)c3c(c2)nnn3C)cc1]
or a pharmaceutically acceptable salt thereof.
* * * * *